(12) United States Patent
Leem et al.

(10) Patent No.: US 11,925,118 B2
(45) Date of Patent: Mar. 5, 2024

(54) LIGHT ACTIVATED PHOTOREACTION VIA GENETIC HYBRIDIZATION OF FAR-RED FLUORESCENT PROTEIN AND SILK

(71) Applicant: Purdue Research Foundation, West Lafayette, IN (US)

(72) Inventors: Jung Woo Leem, West Lafayette, IN (US); Seung Ho Choi, West Lafayette, IN (US); Young L. Kim, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 11 days.

(21) Appl. No.: 17/704,235

(22) Filed: Mar. 25, 2022

(65) Prior Publication Data

US 2022/0271242 A1    Aug. 25, 2022

Related U.S. Application Data

(62) Division of application No. 15/874,864, filed on Jan. 18, 2018, now abandoned.
(Continued)

(51) Int. Cl.
*C12P 1/00* (2006.01)
*A23B 7/015* (2006.01)
(Continued)

(52) U.S. Cl.
CPC ........... *H10K 85/761* (2023.02); *A23B 7/015* (2013.01); *A23B 7/154* (2013.01); *A61L 2/0052* (2013.01); *A61L 2/0076* (2013.01); *A61L 2/084* (2013.01); *A61L 2/088* (2013.01); *A61N 5/062* (2013.01); *A61N 5/0624* (2013.01); *B01D 29/62* (2013.01); *B01D 46/66* (2022.01); *C07K 14/43504* (2013.01); *C07K 14/43586* (2013.01); *C07K 19/00* (2013.01); *C09K 11/06* (2013.01); *H01G 9/2018* (2013.01); *H10K 30/30* (2023.02); *H10K 30/82* (2023.02); *A23V 2002/00* (2013.01); *A61N 2005/0663* (2013.01); *C07K 2319/00* (2013.01);
(Continued)

(58) Field of Classification Search
CPC .... A23B 7/015; A23B 7/154; A23V 2002/00; A61L 2/0052; A61L 2/0076; A61L 2/084; A61L 2/088; A61N 2005/0663; A61N 5/062
USPC .......................................................... 435/41
See application file for complete search history.

(56) References Cited

PUBLICATIONS

Vegh et al., Reactive Oxygen Species in Photochemistry of The Red Fluorescent Protein "Killer Red", ChemComm., 2011, 4887-4889, The Royal Society of Chemistry.*
(Continued)

*Primary Examiner* — Monzer R Chorbaji
(74) *Attorney, Agent, or Firm* — Piroozi-IP, LLC

(57) ABSTRACT

A method of inactivating harmful microorganisms of a filtration medium including pathogenic bacteria and viruses is disclosed which includes placing a predetermined quantity of a hybridized fluorescent silk on to a filtration medium, applying light for a predetermined amount of time to the placed quantity of the hybridized fluorescent silk, and passing a fluid through the medium, wherein the fluid is one of substantially air or substantially water,
wherein the hybridized fluorescent silk is one of KillerRed, SuperNova, KillerOrange, Dronpa, TurboGFP, mCherry, or any combination thereof.

10 Claims, 38 Drawing Sheets
(35 of 38 Drawing Sheet(s) Filed in Color)

Related U.S. Application Data

(60) Provisional application No. 62/593,976, filed on Dec. 3, 2017, provisional application No. 62/448,332, filed on Jan. 19, 2017.

(51) Int. Cl.
| | |
|---|---|
| *A23B 7/154* | (2006.01) |
| *A61L 2/00* | (2006.01) |
| *A61L 2/08* | (2006.01) |
| *A61N 5/06* | (2006.01) |
| *B01D 29/62* | (2006.01) |
| *B01D 46/66* | (2022.01) |
| *C07K 14/435* | (2006.01) |
| *C07K 19/00* | (2006.01) |
| *C09K 11/06* | (2006.01) |
| *H01G 9/20* | (2006.01) |
| *H10K 30/30* | (2023.01) |
| *H10K 30/82* | (2023.01) |
| *H10K 85/00* | (2023.01) |
| *H10K 102/00* | (2023.01) |
| *H10K 102/10* | (2023.01) |

(52) U.S. Cl.
CPC ........ *C09K 2211/14* (2013.01); *H01G 9/2059* (2013.01); *H10K 2102/00* (2023.02); *H10K 2102/102* (2023.02); *H10K 2102/103* (2023.02); *Y02E 10/549* (2013.01)

(56) References Cited

PUBLICATIONS

Mutan Silk Worm NPL, 2013, , WWW,Wired.com/2013/06, Nadia Drake.*
Li Z, Construction of Transgenic Silkworm Spinning Antibacterial Silk With Fluorsecence, 2015, Mol. Bio. Rep.*

* cited by examiner

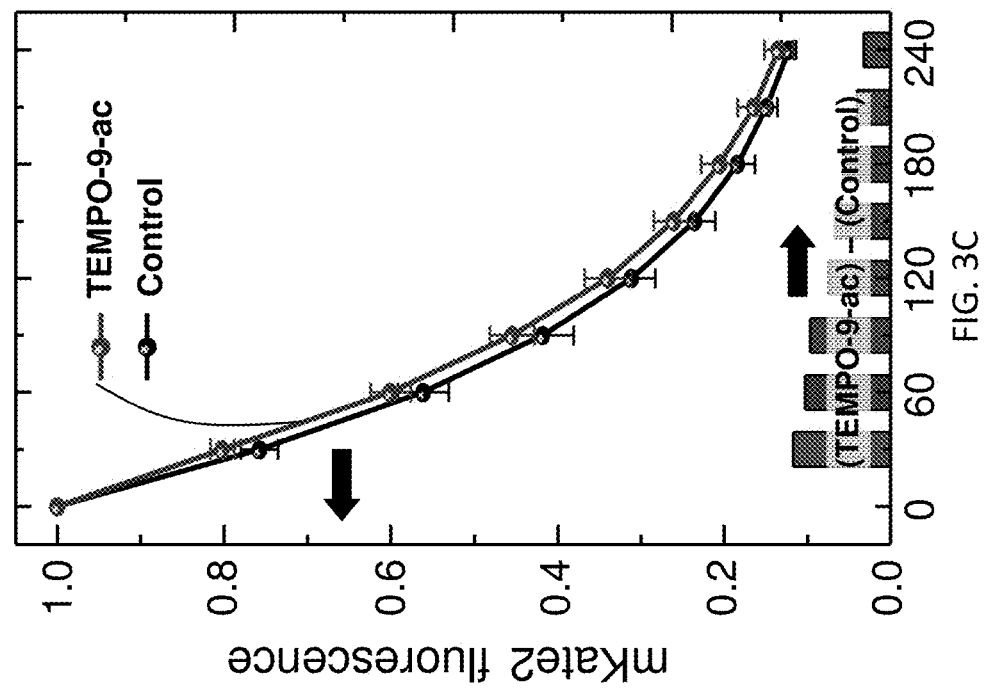

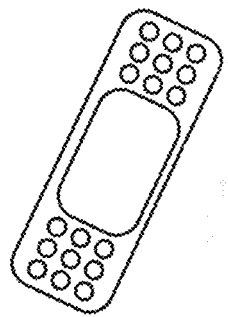
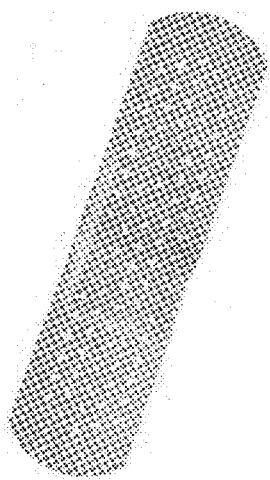
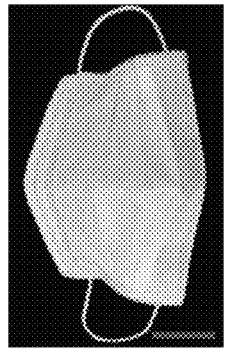
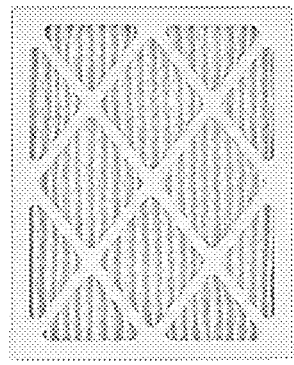
FIG. 5A protective suit
FIG. 5B Mask
FIG. 5C wall paper
FIG. 5D Bandage
FIG. 5E Filter Forms of fluorescent silk polymers for biomedical applications
Polymer (solution, film, mat)

Solution (or gel)-type ointment for wounds

Polymer film

Mask pack

Bandage or patch (or microneedles)

| No | Location | Mr(exp) | Mr(calc) | Sequence |
|---|---|---|---|---|
| 1 | 49-63 | 1590.8493 | 1589.8148 | DASGAVIEEQITTKK |
| 2 | 70-79 | 2442.8413 | 2441.1519 | NHIGILGKNEK |
| 3 | 83-104 | 2442.8413 | 2441.1519 | TFVITTDSDGNESIVEEDVLMK |
| 4 | 159-171 | 1637.3093 | 1637.7462 | MVSELIKENMHMK |
| 5 | 172-184 | 1589.3663 | 1589.7296 | LYMEGTVNNHHFK |
| 6 | 185-201 | 1946.4763 | 1945.8145 | CTSEGEGKPYEGTQTMR |
| 7 | 204-226 | 2433.9883 | 2433.1925 | AVEGGPLPFAFDILATSFMYGSK |
| 8 | 252-279 | 3062.0203 | 3060.4597 | VTTVEDGGVLTATQDTSLQDGCLIYNVK |
| 9 | 280-294 | 1660.4443 | 1660.8242 | IRGVNFPSNGPVMQK |
| 10 | 295-316 | 2350.9313 | 2351.1440 | KTLGWEASTETLYPADGGLEGR |
| 11 | 348-357 | 1270.9383 | 1270.6128 | MPGVYVVDRR |
| 12 | 363-379 | 1973.5673 | 1973.9330 | EADKETYVEQHEVAVAR |
| 13 | 380-386 | 881.6313 | 881.3953 | YCDLPSK |
| 14 | 387-403 | 1826.5823 | 1827.8863 | LGHRPQQVDSVSYGAGR |
| 15 | 404-422 | 1687.4983 | 1685.7604 | GYGQGAGSAASSVSSASSR |
| 16 | 423-429 | 945.4853 | 945.4304 | SYDYSRR |
| 17 | 433-439 | 843.3973 | 843.4385 | KNCGIPR |

FIG. 10A

LIGHT ACTIVATED PHOTOREACTION VIA GENETIC HYBRIDIZATION OF FAR-RED FLUORESCENT PROTEIN AND SILK

CROSS-REFERENCE TO RELATED APPLICATIONS

The present patent application is a divisional application of U.S. Non-Provisional application Ser. No. 15/874,864 filed Jan. 18, 2018 which is related to and claims the priority benefit of U.S. Provisional Patent Application Ser. No. 62/448,332, filed Jan. 19, 2017, and U.S. Provisional Patent Application Ser. No. 62/593,976, filed Dec. 3, 2017, the contents of each of which is hereby incorporated by reference in its entirety into the present disclosure.

STATEMENT REGARDING GOVERNMENT FUNDING

This invention was made with government support under FA2386-16-1-4114 awarded by US Air Force Office of Scientific Research. The government has certain rights in the invention.

TECHNICAL FIELD

The present disclosure generally relates to activation of silk with a fluorescent protein, and in particular, to a genetic hybridization of fluorescent protein and silk used in antimicrobial and antiviral applications.

BACKGROUND

This section introduces aspects that may help facilitate a better understanding of the disclosure. Accordingly, these statements are to be read in this light and are not to be understood as admissions about what is or is not prior art.

The recent advances in plasmonics and nanophotonics have opened a variety of new possibilities to engineer nanomaterials to have properties that do not exist naturally, which is known as metamaterials. Specifically, plasmonic photocatalysis, which requires a combination of semiconductor nanoparticles and metals, has recently facilitated the rapid progress in enhancing photocatalytic efficiency under visible or solar light. Visible light driven plasmonic photocatalysis have resulted in a variety of applications, including hydrogen generation, carbon dioxide reduction, desalination, disinfection, and water/air purification. However, such conventional photocatalysis is intrinsically limited for large-scale, economical, and eco-friendly production.

The phototoxicity of fluorescent proteins, in particular red fluorescent proteins (RFP) is unanimously acknowledged in several different scientific communities; RFP often generates and releases reactive oxygen species (ROS) upon light excitation, while the exact types of ROS vary among different RFP variants. Since the use of conventional RFP was restricted by cytotoxicity, noncytotoxic RFP variants have been successfully developed for whole-cell labeling and cellular imaging in vivo. As an opposite utilization, RFP has also been used as a means of selectively damaging specific proteins upon light activation, which is also known as chromophore-assisted light inactivation. In this case, RFP is recapitulated as 'genetically-encoded ROS-generating proteins' for inactivating target cells and ablating tissue of interest. However, biologically compatible and biodegradable carriers of RFP remain elusive.

As an excellent biomaterial for skin smoothing and regeneration, silk can be used as fabrics or processed into host materials and structures.

Therefore, there is an unmet need for a novel approach and arrangement to utilize proteins capable of generating reactive oxygen species in a biocompatible and biodegradable manner.

SUMMARY

A method of visible light driven-disinfection of a surface of an object exposed or attached to harmful microorganisms including pathogenic bacteria and viruses using a genetically hybridized fluorescent silk is provided. The method includes placing a predetermined quantity of the genetically hybridized fluorescent silk i) directly on to a skin surface of a subject; or ii) on a medium and then placing the medium on the skin surface of the subject. The method further includes applying light in the visible spectrum for a predetermined amount of time to the placed quantity of genetically hybridized fluorescent silk.

Another method of disinfection of a filtration medium of harmful microorganisms including pathogenic bacteria and viruses upon visible light irradiation using a genetically hybridized fluorescent silk, is also disclosed. The method includes placing a predetermined quantity of the genetically hybridized fluorescent silk on to a filtration medium and applying light for a predetermined amount of time to the placed quantity of the genetically hybridized fluorescent silk. The method also includes passing a fluid through the medium, wherein the fluid is one of air or water.

Another method of preserving fruit and/or vegetables is disclosed. The method includes placing a predetermined quantity of a genetically hybridized fluorescent silk i) directly on to a skin surface of a fruit/vegetable; or ii) on a medium and then placing the medium on the skin surface of the fruit/vegetable. The method further includes applying light for a predetermined amount of time to the placed quantity of the genetically hybridized fluorescent silk.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 3C is a fluorescence graph for ABDA for $O_2$ that show reduction in photobleaching of mKate2 silk discs which is quantified by the normalized fluorescent intensity of mKate2 silk in the presence of fluorogenic scavengers of TEMPO-9-ac for $O_2$.

FIGS. 5A-5E are schematics of various embodiments representing applications of mKate2 silk or other variations of the genetically modified silkworm produced silk including protective suits including scrubs, gloves, or other sheet material that can be used in medical and non-medical garment industry (including for burn patients), masks, wallpaper, bandages, and filtration applications.

FIGS. 10A and 10B are sequence listings for peptides from mKate2 and sequence alignment of mKate2/Fibroin H-chain fusion recombinant protein amino acid.

DETAILED DESCRIPTION

Figure 1A:
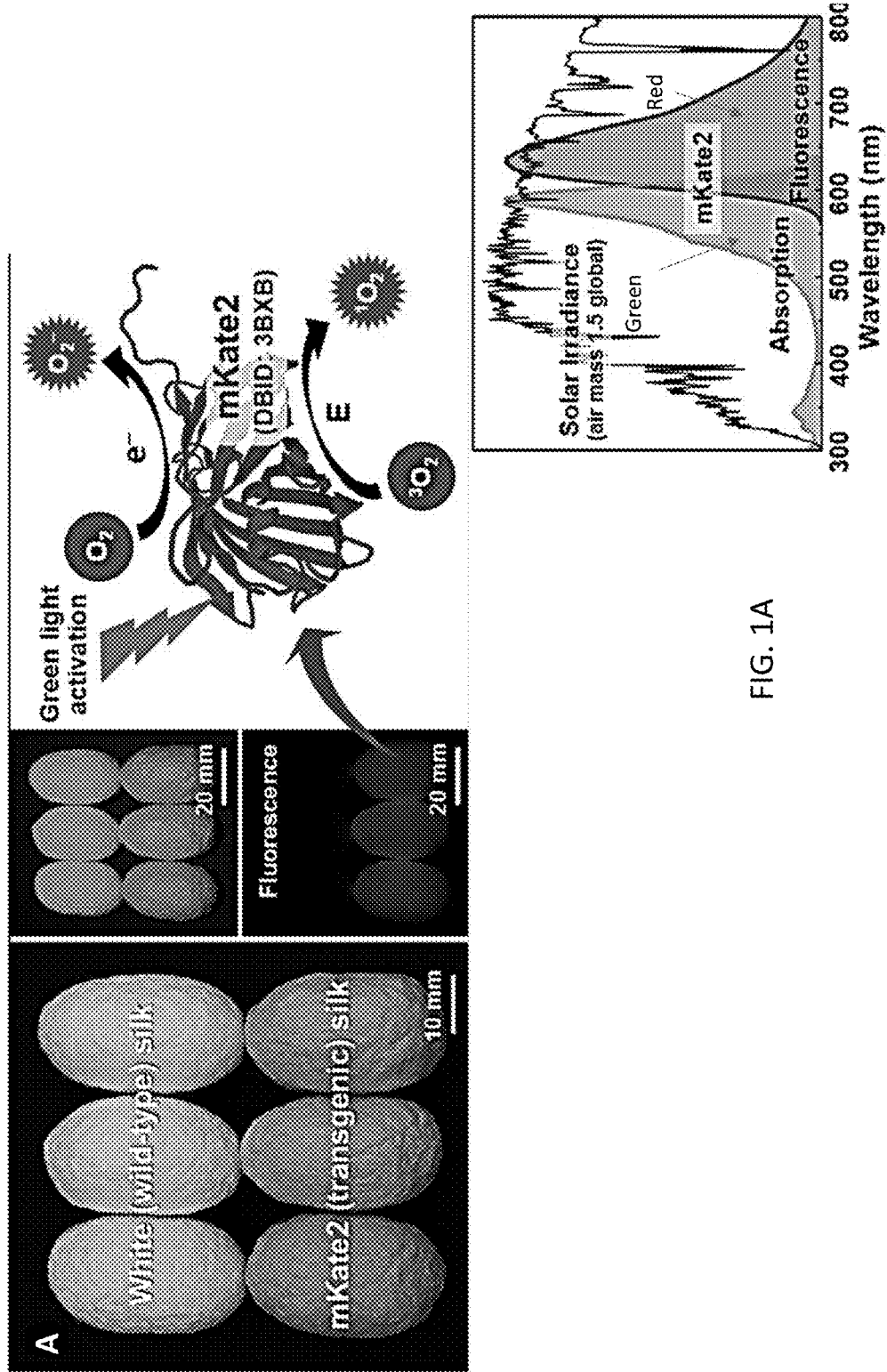
FIG. 1A is a schematic illustration of reactive oxygen species (ROS) generating mKate2 (transgenic) silk cocoons vs. white (wild-type) silk cocoons both under white light and under green light activation.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 90%, within 95%, or within 99% of a stated value or of a stated limit of a range.

In the present disclosure, a hybridization of a photosensitization platform based on mKate2 and silk using genetically engineered silkworms has been disclosed for a variety of novel applications. These applications include biomedical antimicrobial and antiviral applications. Data is presented herein to show how the mKate2 silk can effectively reduce E. coli colonies with exposure to visible light, without using ultra-violet light. Other applications such as wearable and edible arrangement are and data associated with the same are provided to improve human's constant battle against microbial and viral colonies without the use of potentially harmful toxic nanoparticles or carcinogens. Without a need of additional nanoconjugations (e.g. metals, dye molecules, and quantum dots), red fluorescent proteins (RFP) can be excited by solar (visible) and green light, avoiding the most common carcinogen exposure of ultra-violet light. Both fluorescent proteins and silk are degradable and digestible, eliminating the potential risk of exposure and consumption. As a bio-synthesis reactor (i.e. green manufacturing), silkworm transgenesis is known for producing recombinant proteins into silk in large amounts. Silk fibers are easily woven into large-area, continuous, and flexible fabrics using the existing textile manufacturing infrastructure. The unprecedentedly strong light scattering of native silk, which is manifested as the 'silvery' and 'lustrous' reflection, can enhance interactions of light with RFP inside silk fibers.

Fluorescent proteins, in particular red fluorescent proteins often produce phototoxic reactive oxygen radicals, which are considered as a detrimental side effect in cellular imaging or are proactively employed for ablation in cancerous tissue. Additionally, silk produced by silkworms can directly be used as fabrics or processed into host materials and structures.

According to the present disclosure, transgenic fusion of far-red fluorescent protein (mKate2) with silk provides a photosensitization hybridization platform for photoinducibly controlling reactive oxygen species. Taking advantage of green (visible) light activation, native and regenerated mKate2 silk generate superoxide radical and singlet molecular oxygen, in a comparable manner of visible light-driven plasmonic photocatalysis. The genetic expression of mKate2 in silk offers immediately exploitable scalable photocatalyst materials in diverse formats and excludes potentially hazardous effects associated with foreign semiconductor photocatalytic nanomaterials.

The phototoxicity of fluorescent proteins, in particular red fluorescent proteins (RFP) is utilized according to the present disclosure to generate and release reactive oxygen species (ROS) upon light excitation. Noncytotoxic RFP variants have been successfully developed for whole-cell labeling and cellular imaging in vivo. As an opposite utilization, RFP has also been used as a means of selectively damaging specific proteins upon light activation, which is also known as chromophore-assisted light inactivation. In this case, RFP is recapitulated as 'genetically-encoded ROS-generating proteins' for inactivating target cells and ablating tissue of interest. All of these characteristics of RFP make RFP a good candidate to replace the use of semiconductor nanocrystals or conjugated nanoparticles for photocatalysis.

Some fluorescent proteins participate in Type I and Type II photosensitization reactions involving the generation of ROS. Predominant free radicals generated by fluorescent proteins depend on the type of photosensitization reactions and the concentration of local molecular oxygen (i.e. electron acceptor). For example, (enhanced) green fluorescent protein, (E)GFP typically produces singlet oxygen ($^1O_2$) via Type II reaction, in which energy transfer occurs from the excited triplet state of the fluorescent protein to molecular oxygen. RFP such as KillerRed can undergo Type I photosensitization reaction, in which electron transfer to molecular oxygen yields superoxide ($O_2^{\cdot-}$). Another advantageous aspect of ROS resulting from Type I and Type II reactions is that the migration (or damage) distance ranges from 1.5 nm to 200 nm. The enhanced diffusion distance and lifetime of singlet oxygen can serve more selective radical species, rather than being instantaneously reactive. Importantly, the resultant ROS (i.e. $O_2^{\cdot-}$ and in particular $^1O_2$) generated by plasmonic photocatalysis using visible light are the same as that of RFP photosensitization reactions.

According to the present disclosure, biological hybridization of far-red fluorescent proteins and some natural proteins (i.e. silk) is disclosed for a new class of genetically encoded photosensitization activated using visible (or solar) light, directly producing selective radical species. Direct detection of ROS is known to be highly challenging, because ROS is extremely reactive and unstable. Thus, a novel approach involving turn-on/off fluorescent probes and physical quenchers/scavengers to experimentally validate ROS generated by transgenic RFP silk upon green light activation is also disclosed. Further, transgenic RFP silk can be mass-produced by scalable and continuous manufacturing. Using the polymeric nature of silk, transgenic RFP silk is also processed into nanomaterials and nanostructures in a variety of forms. This approach can overcome the limitation of potential adverse effects associated with foreign synthesized nanoparticles.

Silk produced by silkworms has extensively been utilized as fabrics and processed into engineered biomaterials due to its various merits of the superior mechanical and optical properties as well as the biocompatibility and biodegradability. According to the present disclosure, genetically engineered domesticated silkworms are used to generate the biomaterial of interest. The transgenes of interests are expressed by germline transformation using the gene splicing method piggyBac, known to a person having ordinary skill in the art. This silkworm transgenesis method yields transformed animals for multiple successive generations and produces recombinant substances in large amounts. Silkworm transgenesis readily produces natural photocatalyst and photosensitizer materials in an eco-friendly manner, minimizing the use of industrial facilities. Regarding ecological hazard, transgenic silkworms are highly unlikely to pose threats to natural ecosystems, because silkworms are dependent on humans for survival and reproduction as a completely domesticated indoor insect.

mKate2, which is a far-red monomeric fluorescent protein, was chosen as the transgenic RFP silk. Referring to FIG. 1A, a schematic illustration of ROS generating mKate2 (transgenic) silk cocoons vs. white (wild-type) silk cocoons is shown both under white light and under green light activation. When light shines on mKate2 silk, dye molecules become excited from their ground state to a higher energy state, thereby releasing electrons. Oxygen molecules in presence of free electrons go through a reductive reaction ($O_2 \rightarrow O_2^-$) thereby generating reactive oxygen species (ROS) of superoxide ($O_2^{\cdot-}$) radical and singlet molecular oxygen ($^1O_2$), as shown in FIG. 1A. Also shown in FIG. 1A is a spectral output showing mKate2 energy as a function of light wavelength in nm. The AM 1.5 Standard spectrum refers to a standard terrestrial solar spectrum. The green and the red curves presents the absorption spectrum and the fluorescent emission spectrum of mKate2. Thus, mKate2 is activated by solar light.

Green light belongs to the peak wavelength range of the solar spectrum. From a phototoxicity standpoint, mKate and mKate2 are widely considered as one of the cytotoxic standards. From a protein structural standpoint, the phototoxic action of mKate is commonly acknowledged to originate from a cleft-like opening channel filled with water molecules inside, allowing for enhanced generation and release of ROS. Specifically, mKate has a cleft-like β-barrel frame between β sheets (β7 and β0), resulting in relatively high phototoxicity. Several other fluorescent proteins, including KillerRed, SuperNova, KillerOrange, Dronpa, TurboGFP, and mCherry, have similar a β-barrel structure with a water-filled pore, which can also be used to tune the excitation wavelength range and to select the photosensitization properties.

Figure 1B:
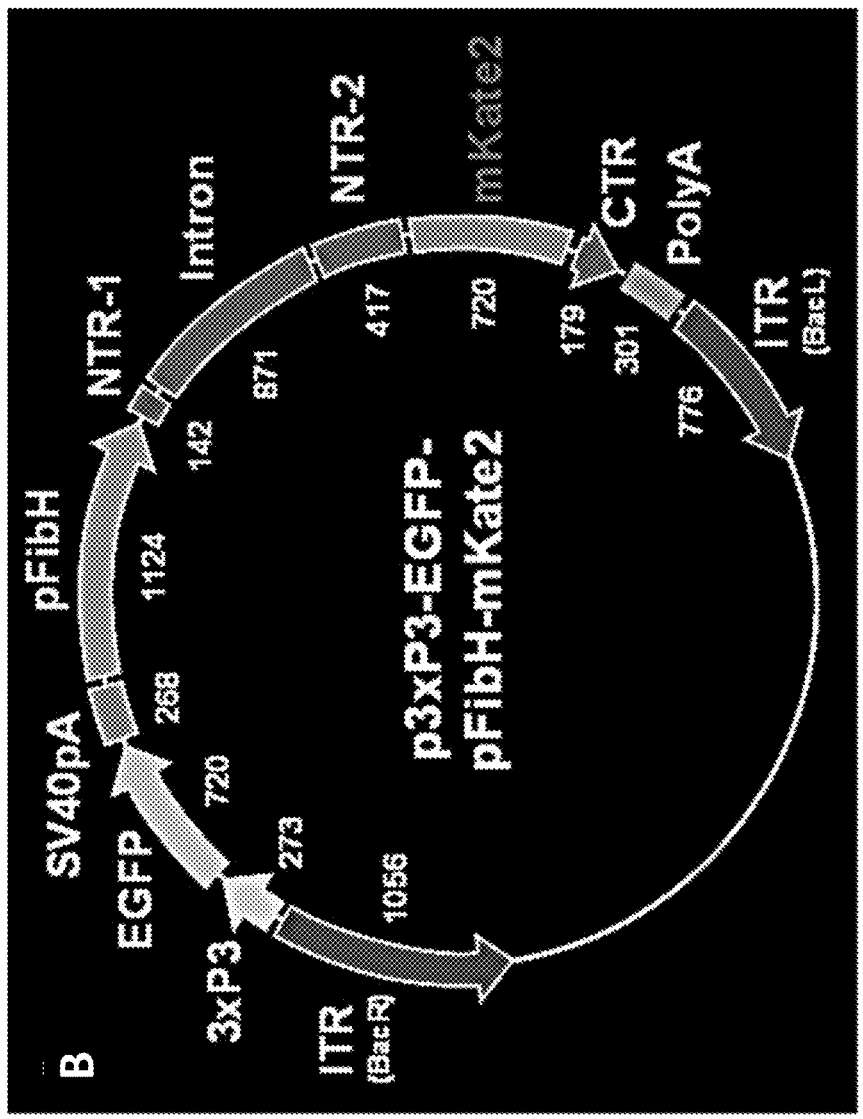
FIG. 1B is a schematic representing construction of transfer vector p3xP3-EGFP-pFibH-mKate2 for mKate2 silkworm transgenesis.
Figure 1C:
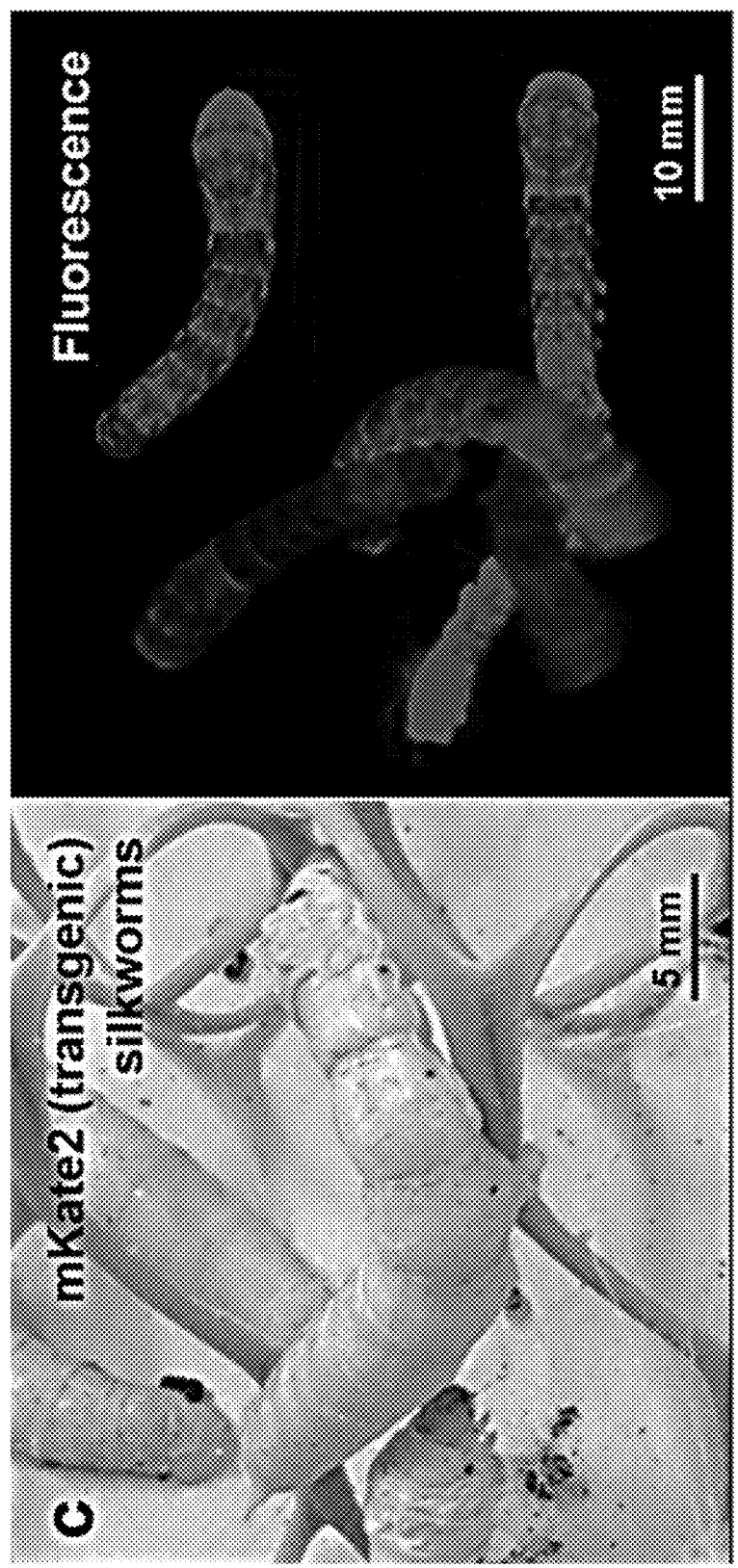
FIG. 1C is a photograph (left) and fluorescent image (right) of the silk gland for the transgenic mKate2 silkworm larvae at the 3rd day of the 5th instar.
Figure 9:
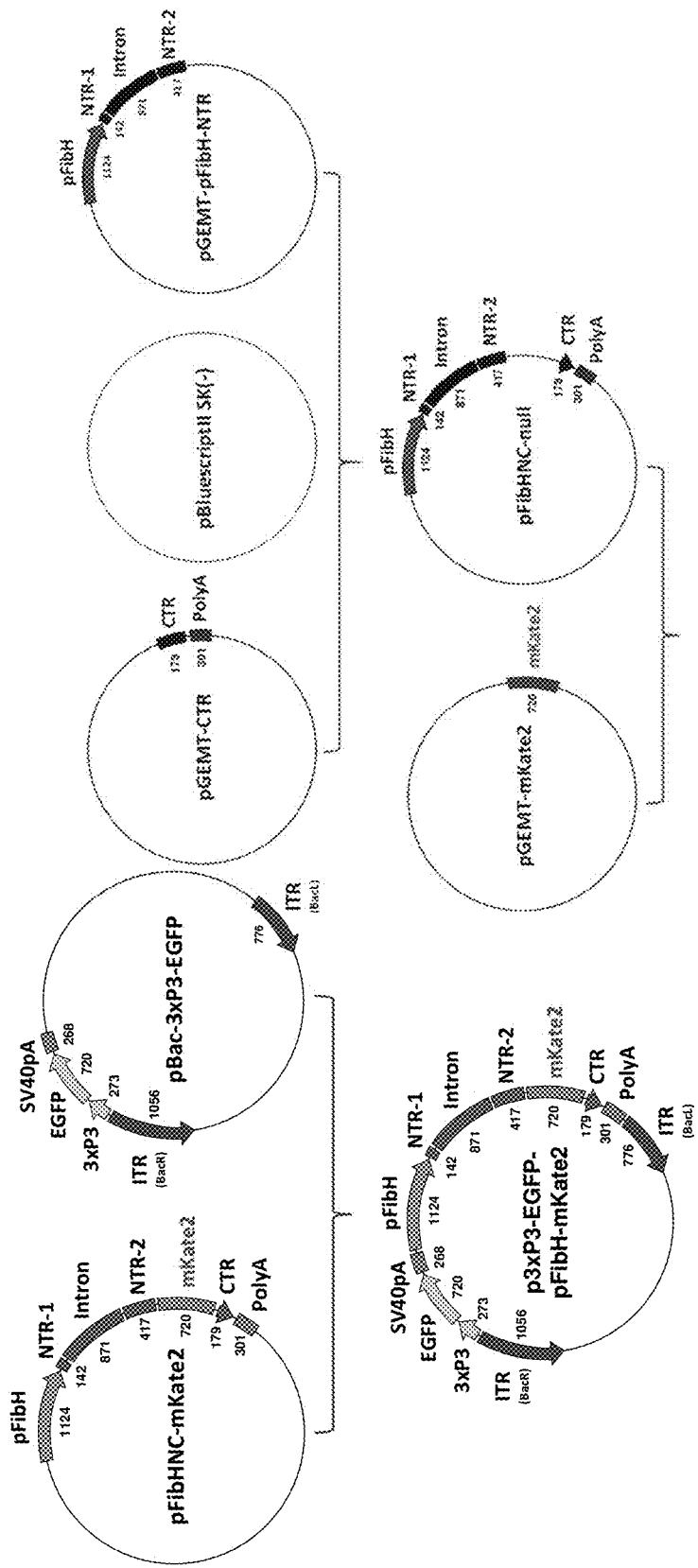
FIG. 9 is a schematic showing a nucleotide sequences of pFibH-NTR and CTR derived from Genebank Accession No. AF226688. pFibH: fibroin heavy chain promoter domain (1124 bp), NTR-1: N-terminal region 1 (142 bp), intron: first intron (871 bp), NTR-2: N-terminal region 2 (417 bp), CTR: Cterminal region (179 bp), PolyA: poly(A) signal region (301 bp), EGFP: enhanced green fluorescent protein gene, mKate2: monomeric far-red fluorescent protein, ITR (BacR, BacL): inverted repeat sequences of piggyBac arms, 3xP3: 3xP3 promoter, and SV40: SV40 polyadenylation signal sequence.
Figure 11:
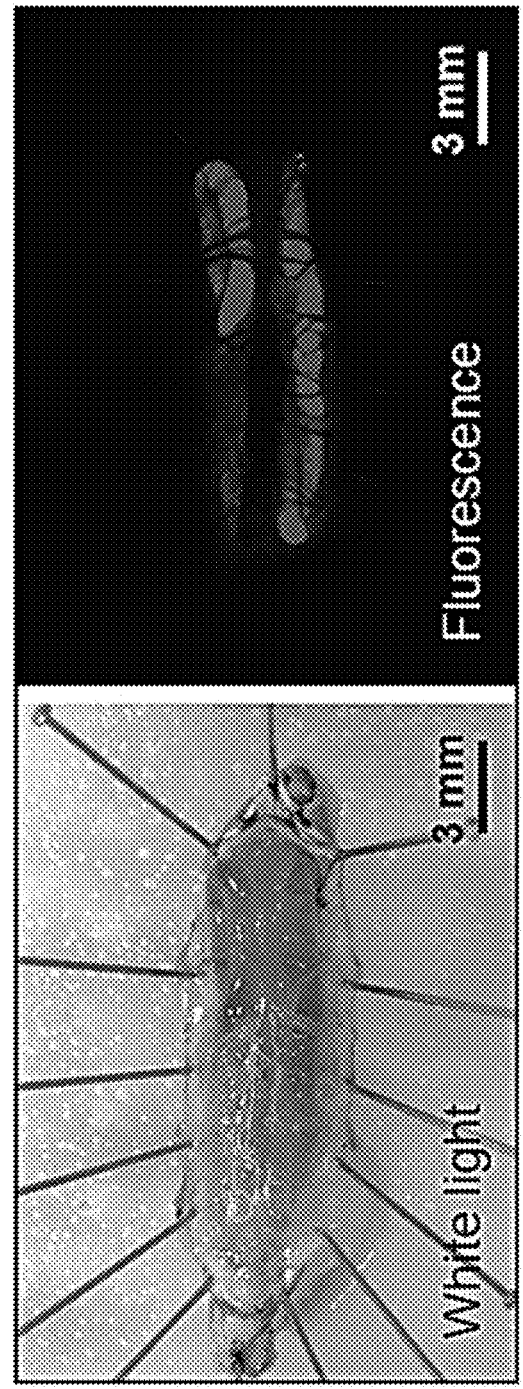
FIG. 11 is photograph (left) and fluorescent image (right) of the silk gland for the transgenic mKate2 silkworm larvae at the 3rd day of the 5th instar.

Referring to FIG. 1B, a schematic representing construction of transfer vector p3xP3-EGFP-pFibH-mKate2 for mKate2 silkworm transgenesis is shown. For hybridization of mKate2 and silk, mKate2 gene is fused with N-terminal and C-terminal domains of the fibroin heavy chain promoter (pFibH); p3xP3-EGFP-pFibH-mKate2 is the constructed transformation vector Referring to FIG. 9, a schematic is provided showing a nucleotide sequences of pFibH-NTR and CTR are derived from Genebank Accession No. AF226688. pFibH: fibroin heavy chain promoter domain (1124 bp), NTR-1: N-terminal region 1 (142 bp), intron: first intron (871 bp), NTR-2: N-terminal region 2 (417 bp), CTR: Cterminal region (179 bp), PolyA: poly(A) signal region (301 bp), EGFP: enhanced green fluorescent protein gene, mKate2: monomeric far-red fluorescent protein, ITR (BacR, BacL): inverted repeat sequences of piggyBac arms, 3xP3: 3xP3 promoter, and SV40: SV40 polyadenylation signal sequence. 3xP3-EGFP is only for screening a large number of G1 broods, because EGFP fluorescent signals are easily monitored in the stemmata and nervous system at early embryonic and larval stages. Referring to FIGS. 1C and 11, photographs (left) and fluorescent images (right) of the silk gland for the transgenic mKate2 silkworm larvae at the 3rd day of the 5th instar are provided. The silk gland of genetically-encoded mKate2 silkworms is fluorescent.

Figure 10B:
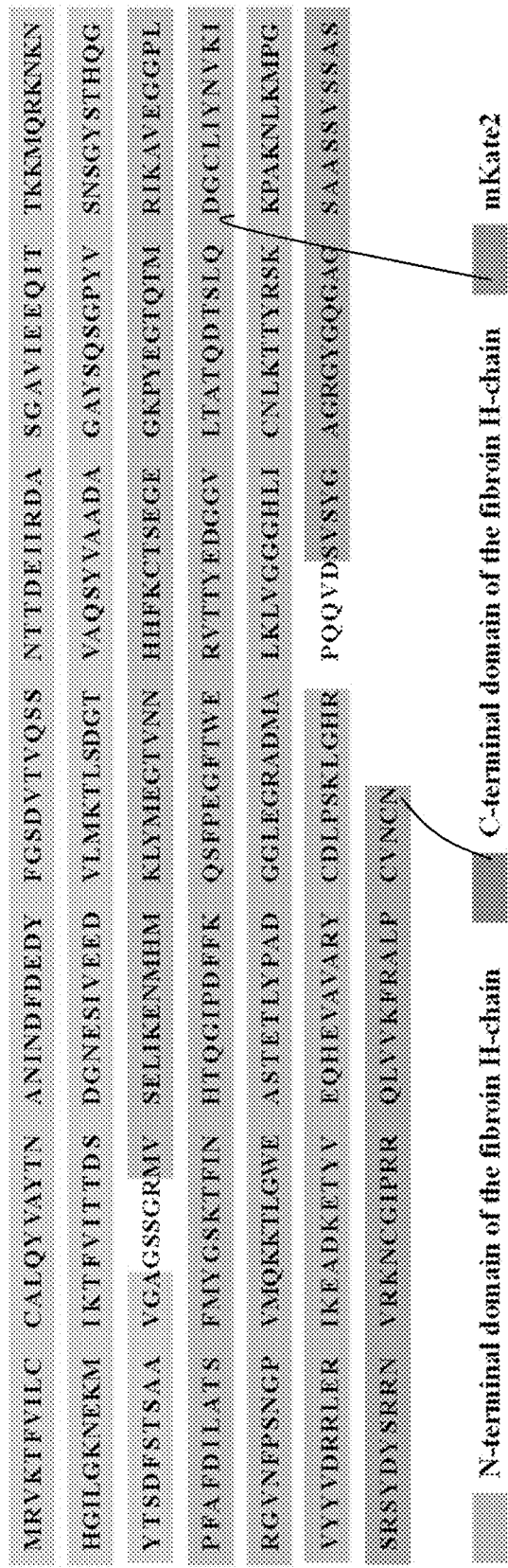

The homogenous production of mKate2 silk results in a mass density of ~12.6% mKate2/Fibroin H-chain fusion recombinant protein. In FIG. 1A, white (wild-type) silk cocoons are not fluorescent, while mKate2-expressing silk cocoons are fluorescent at excitation of $\lambda_{ex}$=543 nm. Referring to FIGS. 10A and 10B, shown are sequence listings for peptides from mKate2 and sequence alignment of mKate2/Fibroin H-chain fusion recombinant protein amino acid. The surface morphologies of silk cocoons were imaged using a scanning electron microscopy (SEM) system (FEI Quanta 3D FEG; Oregon, USA) at 10 keV. In exploiting the fluorescence emission of mKate2 silk, we also performed confocal imaging using an Olympus Fluoview FV1000 confocal laser scanning system adapted to an Olympus IX81 inverted microscope with a 20×UPlanSApo water immersion objective (Olympus, Tokyo, Japan). A green laser excitation source ($\lambda_{ex}$=543 nm) was used with a detection bandpass of 600-700 nm. The typical configuration of confocal microscopy can be summarized as follows: confocal aperture size=50 µm (i.e. ~0.5 airy unit), NA=0.4, and scan speed (pixel dwell time)=10 µs/pixel. 43 image slices were stacked with a slice thickness of 5 µm along the z-axis, covering an area up to ~1270×1270 µm². The three-dimensional (3D) stacked image was also visualized using Imaris 5.0.

Figure 12A:
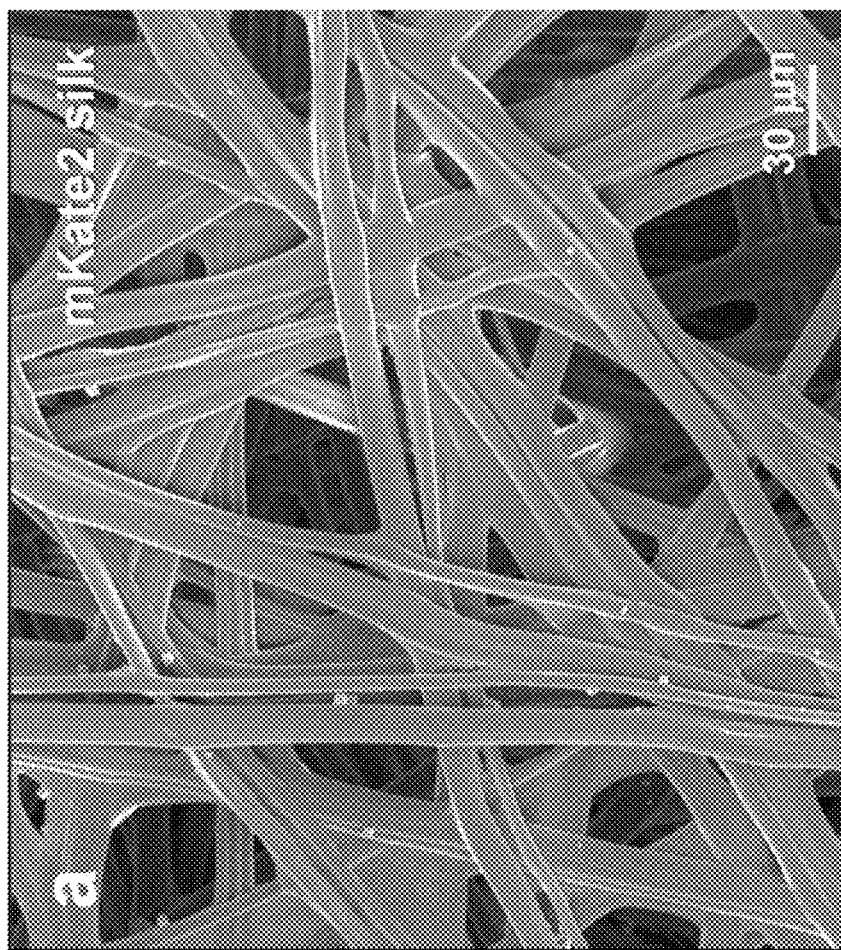
FIGS. 12A, 12B, and 12C include an SEM image of mKate2 silk fibers (FIG. 12A); and confocal fluorescence microscopy images of mKate2 silk fibers under green light excitation (FIGS. 12B and 12C).
Figure 12B:
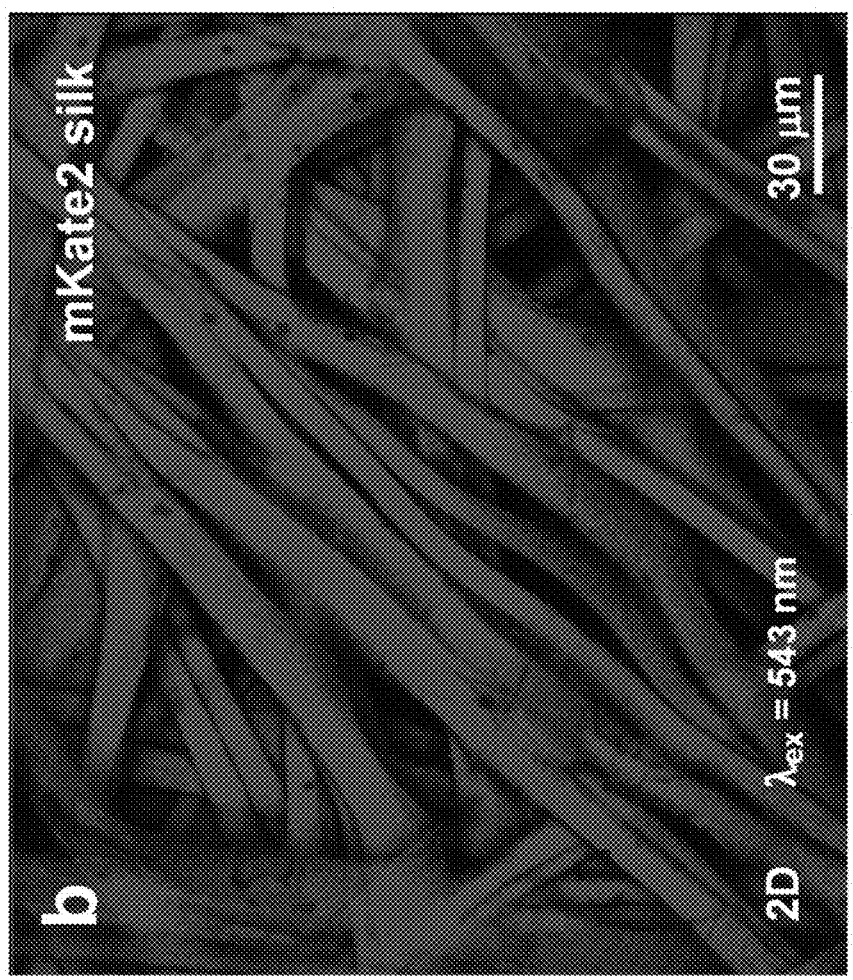
Figure 12C:
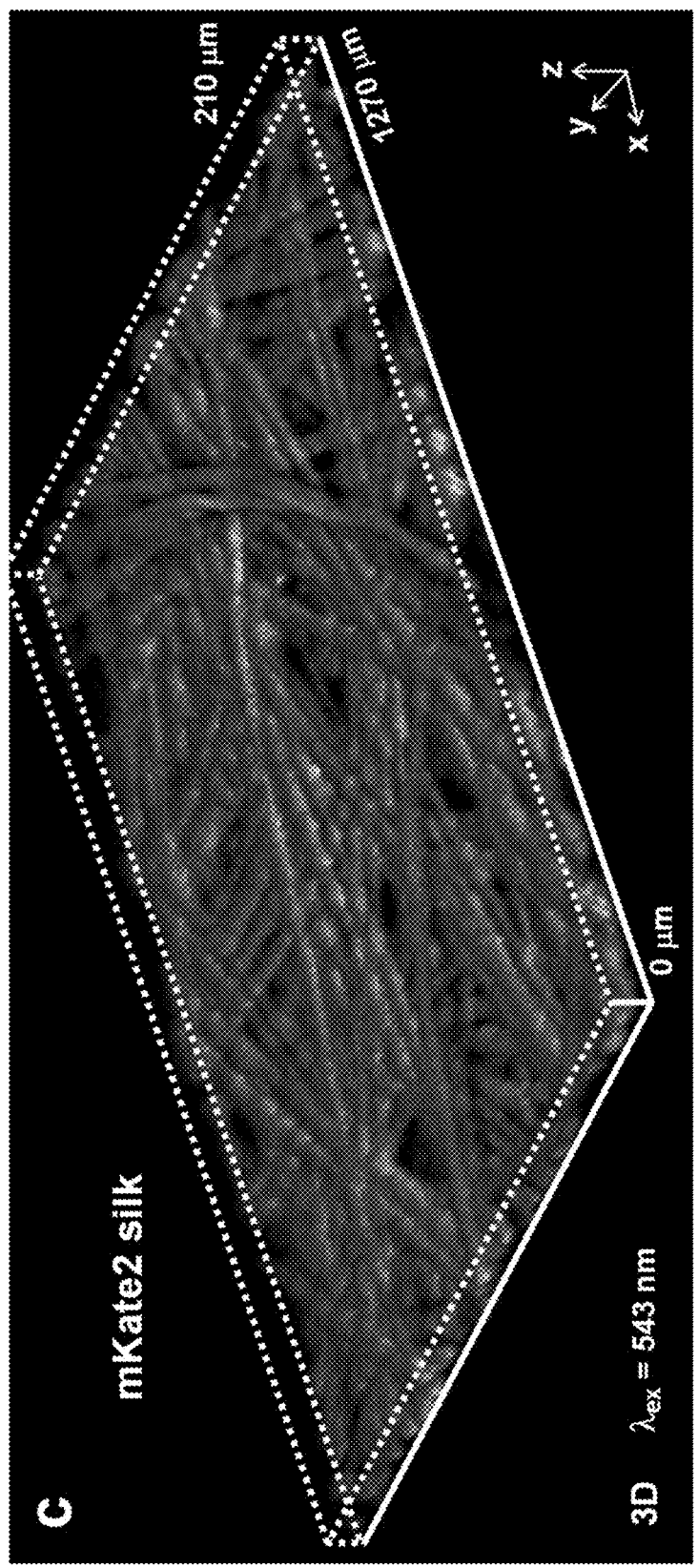

Referring to FIGS. 12A, 12B, and 12C, an SEM image of mKate2 silk fibers (FIG. 12A); confocal fluorescence microscopy images of mKate2 silk fibers under green light excitation (FIGS. 12B and 12C), are provided. Mass density of mKate2/Fibroin H-chain fusion recombinant protein in the transgenic mKate2 silk is estimated to be ~12.6%.

Figure 2A:
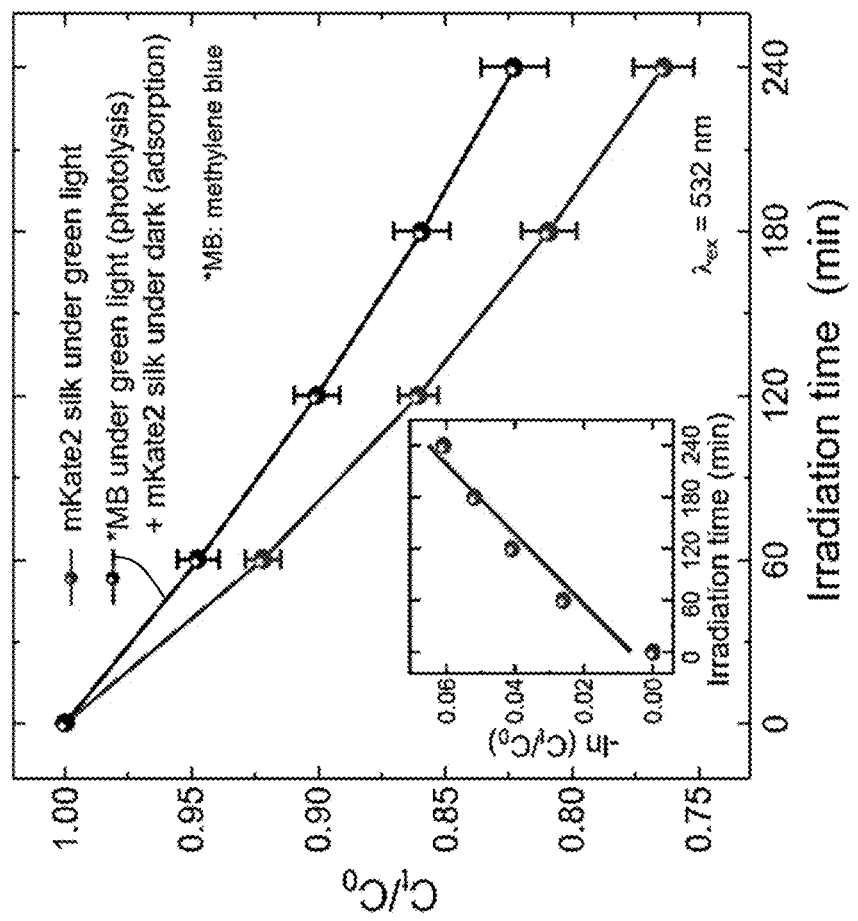
FIG. 2A is a graph of $C_t/C_0$ vs. irradiation time (in minutes) where $C_0$ and $C_t$ denote the initial concentration and reaction concentration, respectively.
Figure 13:
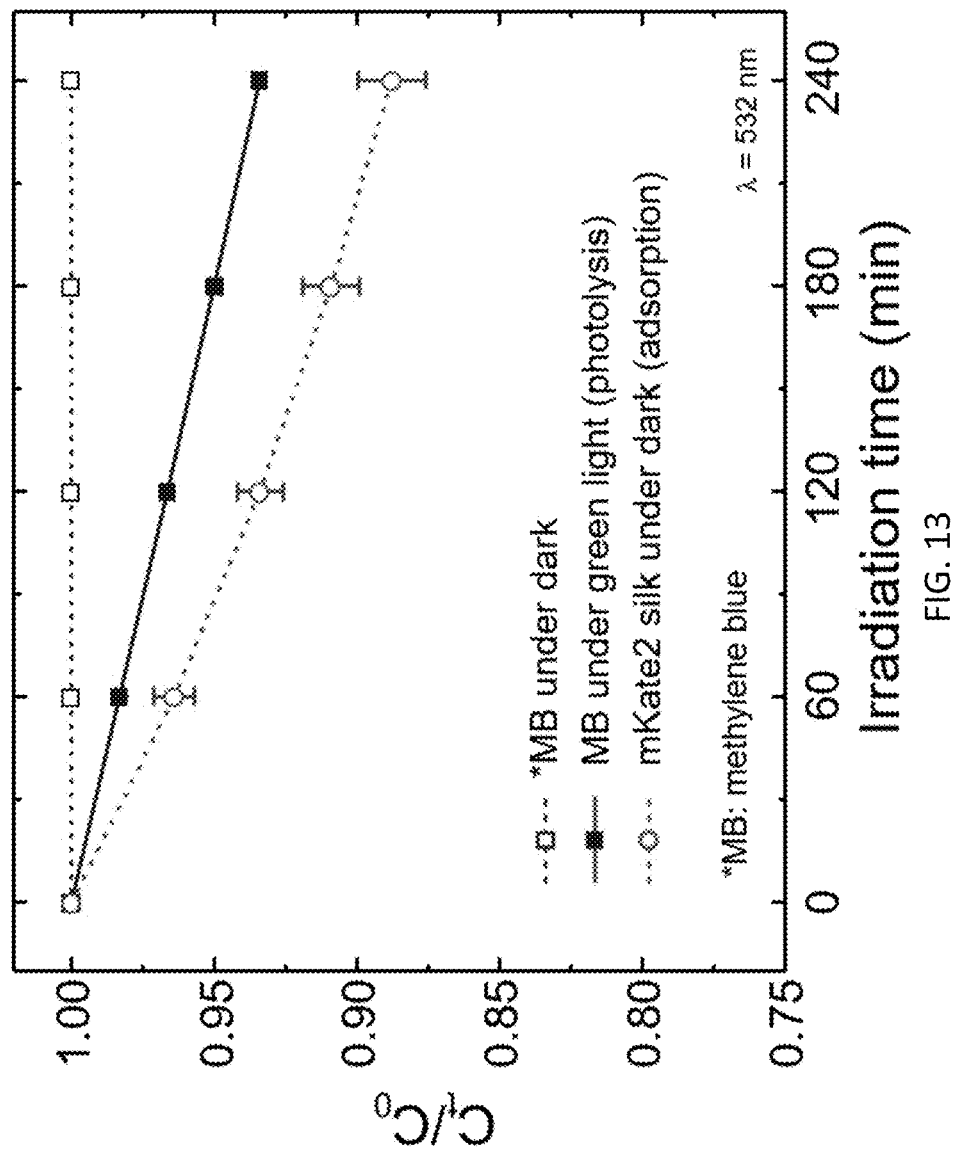
FIG. 13 is a graph of $C_t/C_0$ vs. irradiation time (in min), which represent confounding factors in photodegradation of methylene blue by mKate2 silk.

FIG. 2A, is a graph of $C_t/C_0$ vs. irradiation time (in minutes) where $C_0$ and $C_t$ denote the initial concentration and reaction concentration, respectively. FIG. 2A represents a photometrical analysis of the photocatalytic activity of mKate2 silk for degrading organic blue dye molecules (i.e. methylene blue) in an aqueous solution under green laser light activation ($\lambda_{ex}$=532 nm and optical intensity≈0.2 mW/mm²) at the ambient room temperature. Although this method is not specific to particular types of ROS, degradation of methylene blue is standardly used to validate photocatalysis. Silk has a strong affinity to organic molecules and metal ions. Loss of blue color in a methylene blue solution containing mKate2 silk discs is attributable to infiltration of methylene blue to silk fibers as well as photolysis of green light. Referring to FIG. 13, a graph of $C_t/C_0$ vs. irradiation time (min) under different light irradiation is provided. Adsorption of methylene blue to mKate2 silk and photolysis of methylene blue under green light irradiation is shown in FIG. 13, which represent Confounding factors in photodegradation of methylene blue by mKate2 silk. The error bars represent standard deviations. Thus, separate degradation measurements are performed to account for the adsorption of methylene blue to silk under a dark condition (i.e. no light irradiation) and the photolysis of methylene blue itself without any silk discs. After factoring out these confounding effects, the contribution of ROS generated by the mKate2 silk discs is significant; a linear fit between $\ln(C_t/C_0)$ of mKate2 silk and the irradiation time t results in an apparent pseudo-first-order rate constant ($k_{app}$) value of 2.46×10⁻⁴ min⁻. The inset in FIG. 2A represents a kinetic plot for methylene blue degradation by mKate2 silk after factoring out both adsorption of methylene blue to mKate2 silk and photolysis of methylene blue under green light irradiation. The error bars are standard deviations.

Figure 2B:
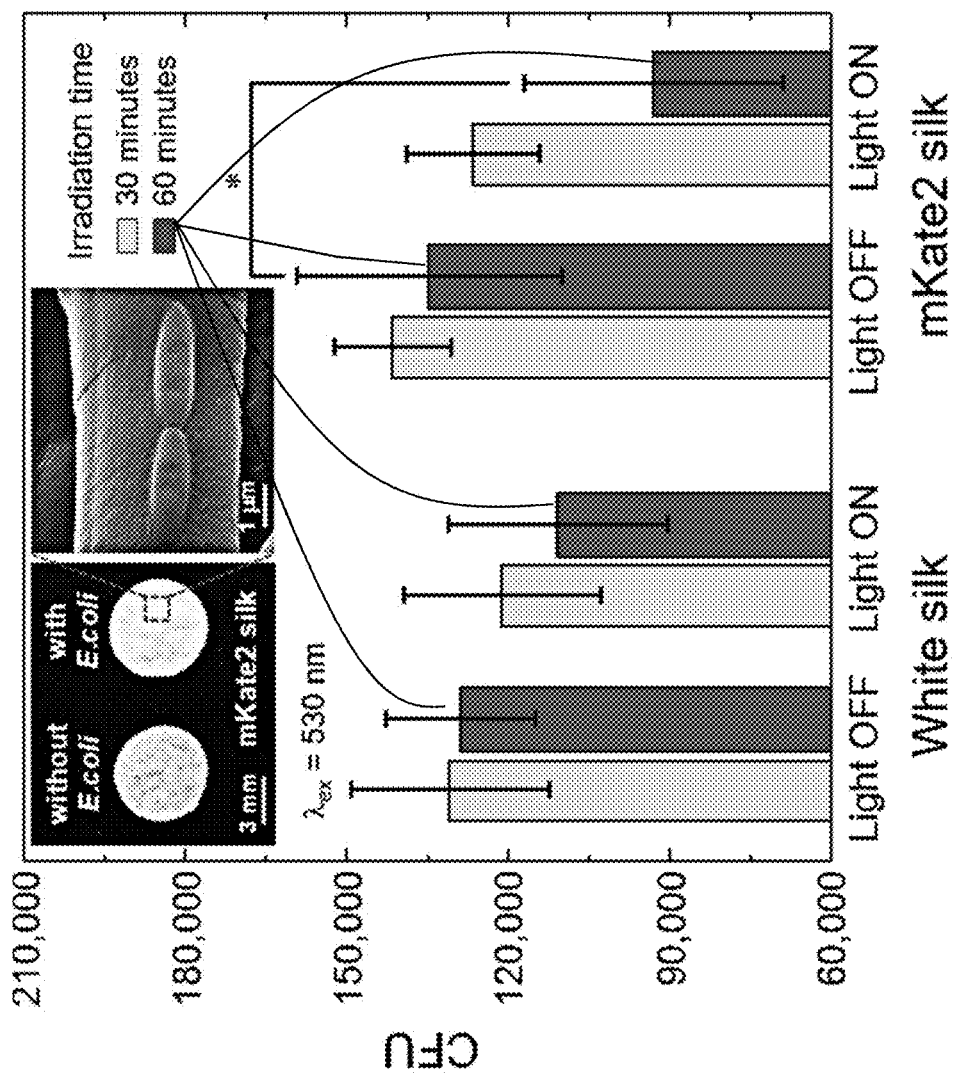
FIG. 2B is a bar graph of colony-forming units (CFU) of live E. coli (DH5α) which are counted in white silk and mKate2 silk discs with and without weak green LED light activation for different irradiation periods of 30 and 60 minutes in a bar graph of CFU vs. white silk and mKate2 silk for different irradiation schemes.

As a model system of testing ROS production, the phototoxicity of mKate2 silk on Escherichia coli (E. coli) upon green light activation was also examined. Referring to FIG. 2B, colony-forming units (CFU) of live E. coli (DH5a) which are counted in white silk and mKate2 silk discs with and without weak green LED light activation for different irradiation periods of 30 and 60 minutes in a bar graph of CFU vs. white silk and mKate2 silk for different irradiation schemes. The inset represents photograph of mKate2 silk discs with and without E. coli and SEM image of mKate2 silk attached with E. coli before light irradiation. Only statistically significant reduction in the survival of E. coli occurs between irradiated (Light ON) and unirradiated (Light OFF) mKate2 silk for 60 minutes (multiple comparison p-value=0.031).

The error bars represent standard deviations from 3 assays with 4 replicates (12 samples) in each group. Historically, ROS generated from conventional photocatalysis has extensively been validated by demonstrating their antimicrobial activities. After DH5α E. coli cells are attached on silk discs (Inset of FIG. 2B), illumination from easily accessible green LED light ($\lambda_{ex}$=530 nm with a FWHM of 30 nm and optical intensity≈0.02 mW/mm²), which is ~10 times weaker than that of the green laser above, is irradiated on the surfaces of white silk and mKate2 silk for 30-60 minutes at the ambient room temperature. Such green light activation can not only be accessible from sunlight, but also belongs to the peak solar radiation spectrum. Dark controls are also maintained without any light irradiation. In FIG. 2B, colony-forming unit (CFU) counts show a statistically significant difference only in bacterial inactivation between irradiated (Light ON)

and unirradiated (Light OFF) mKate2 silk for 60 minutes (multiple comparison p-value=0.031), as seen in tables S1 and S2, provided below. Additional data for multiple comparison tests of white silk and mKate2 silk with and without weak green LED light activation for irradiation times of 30 and 60 minutes are provided below in Tables S1 and S2 below. The survival of *E. coli* from mKate2 silk under weak green light activation (Light ON) is reduced to 45%, compared with the corresponding dark controls (Light OFF). This result supports the idea of green-light-activated genetically encoded photosensitization as an alternative ROS generation route, completely avoiding the use of photocatalytic semiconductor nanoparticles.

TABLE S1

Multiple comparison tests of white silk and mKate2 silk with and without weak green LED light activation (irradiation time = 30 minutes)

| Colony forming unit (CFU) | Mean difference | t | p-value | 95% CI | |
|---|---|---|---|---|---|
| White silk + Light OFF vs. White silk + Light ON | −9,683 | −0.77 | 0.472 | −3,6252 | 16,885 |
| mKate2 silk + Light OFF vs. White silk + Light ON | 10,692 | 0.85 | 0.398 | −14,573 | 35,957 |
| mKate2 silk + Light ON vs. White silk + Light ON | −4,317 | −0.34 | 0.732 | −29,582 | 20,948 |
| mKate2 silk + Light OFF vs. White silk + Light ON | 20,375 | 1.63 | 0.145 | −7,049 | 47,799 |
| mKate2 silk + Light ON vs. White silk + Light ON | 5,367 | 0.43 | 0.671 | −19,898 | 30,632 |
| mKate2 silk + Light OFF vs. mKate2 silk + Light ON | −15,008 | −1.2 | 0.266 | −41,577 | 11,560 |

TABLE S2

Multiple comparison tests of white silk and mKate2 silk with and without weak green LED light activation (irradiation time = 60 minutes)

| Colony forming unit (CFU) | Mean difference | t | p-value | 95% CI | |
|---|---|---|---|---|---|
| White silk + Light OFF vs. White silk + Light ON | −17,967 | −1.04 | 0.305 | −52,859 | 16,926 |
| mKate2 silk + Light OFF vs. White silk + Light ON | 5,884 | 0.34 | 0.736 | −29,009 | 40,776 |
| mKate2 silk + Light ON vs. White silk + Light ON | −35,850 | −2.07 | 0.055 | −72,543 | 843 |
| mKate2 silk + Light OFF vs. White silk + Light ON | 23,850 | 1.38 | 0.201 | −12,843 | 60,543 |
| mKate2 silk + Light ON vs. White silk + Light ON | −17,883 | −1.03 | 0.307 | −52,776 | 17,009 |
| mKate2 silk + Light OFF vs. mKate2 silk + Light ON | −41,733 | −2.41 | *0.031 | −79,607 | −3,860 |

Figure 2C:
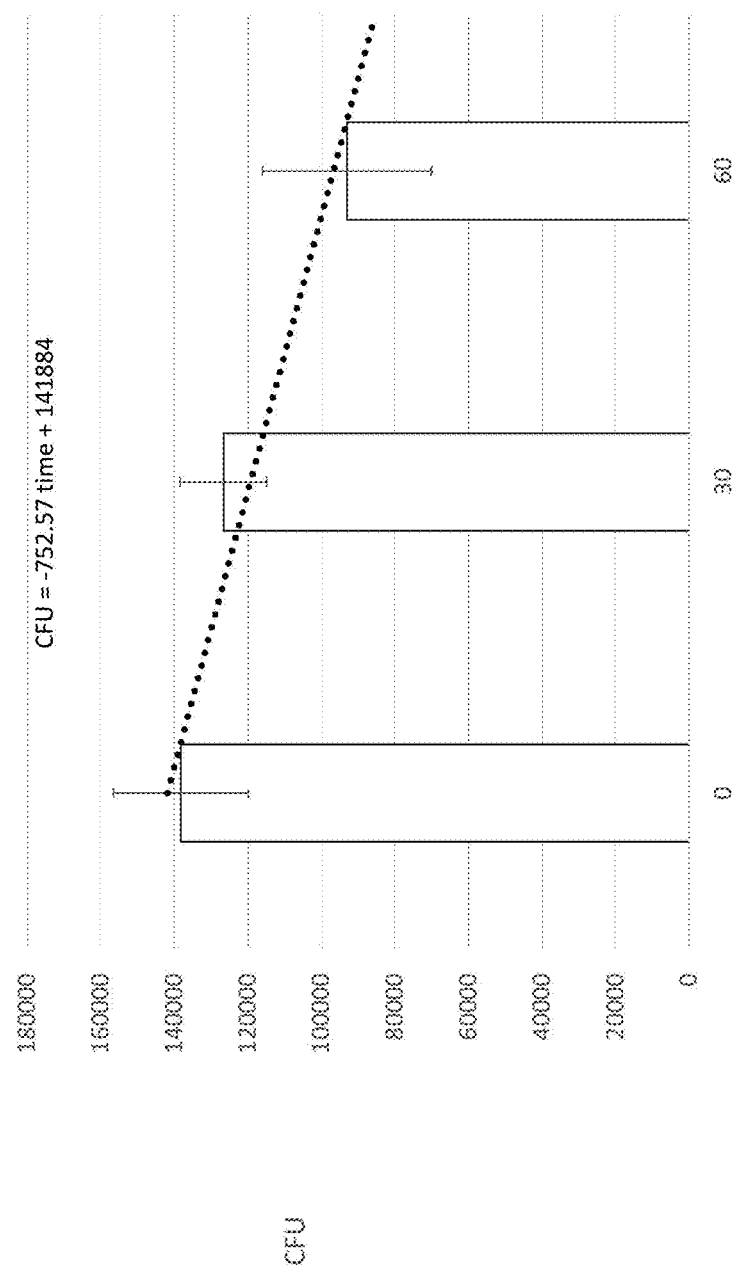
FIG. 2C is a graph of CFU vs. irradiation time in minutes.

Referring to FIG. 2C, a graph of CFU is presented vs. irradiation time in minutes. A first order approximation of reduction of *E. coli* colony-forming unit with irradiation of mKate2 silk produces substantially a linear function shown in FIG. 2C. The function is $$CFU = -752.57 \text{ time} + 141884,$$

where the negative slope is about −752.57, starting point of about 141884, and where time is measured in minutes.

Figure 3A:
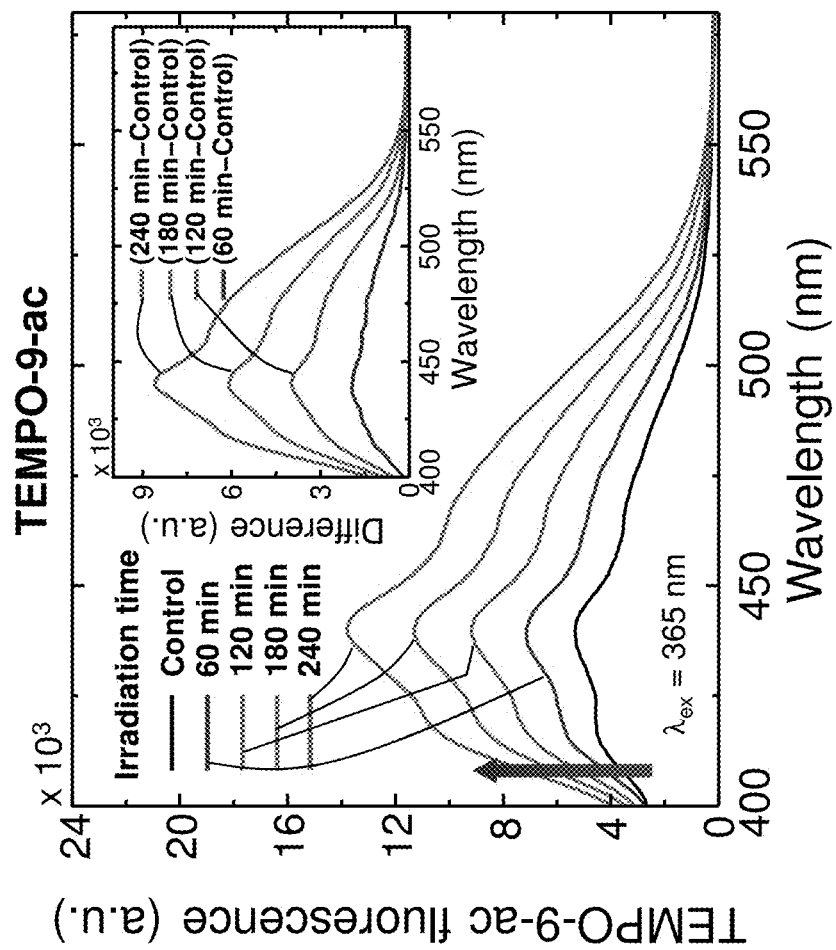
FIG. 3A is a graph of fluorescence of $O_2^{\cdot-}$ mediated by Type I photosensitization reaction, captured by turn-on fluorescent signals of TEMPO-9-ac.
Figure 3B:
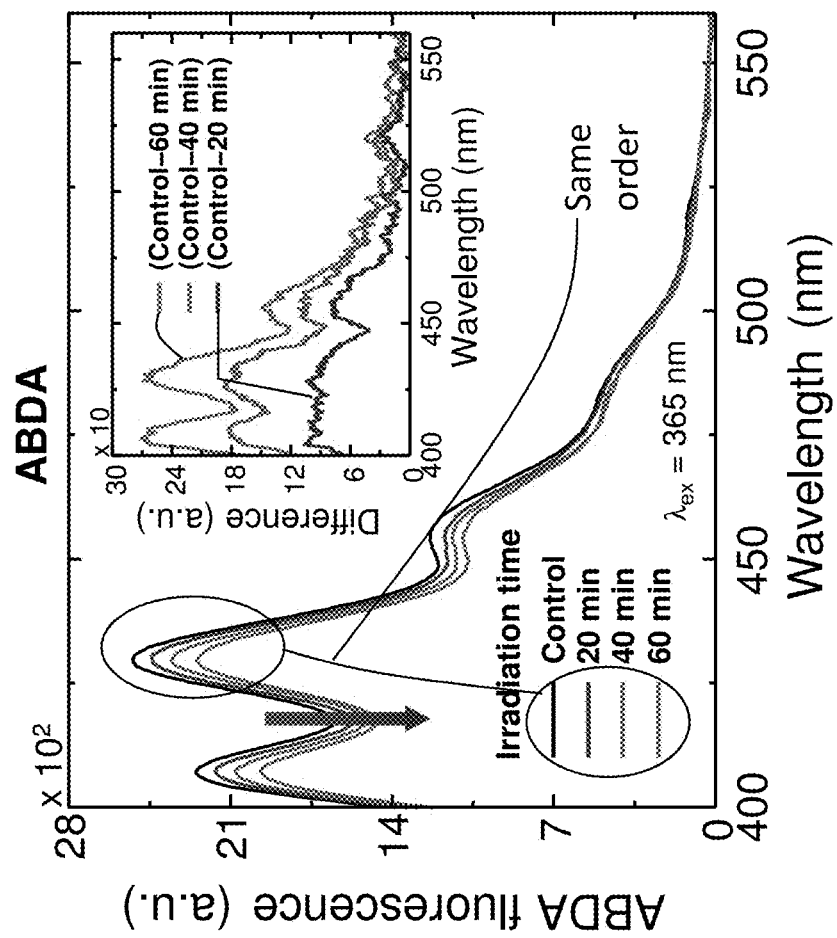
FIG. 3B is a fluorescence graph in which $O_2$ mediated by Type II photosensitization reaction is detected by reduction of the original 9,10-Anthracenediyl-bis(methylene)dimalonic acid (ABDA) fluorescence.
Figure 3D:
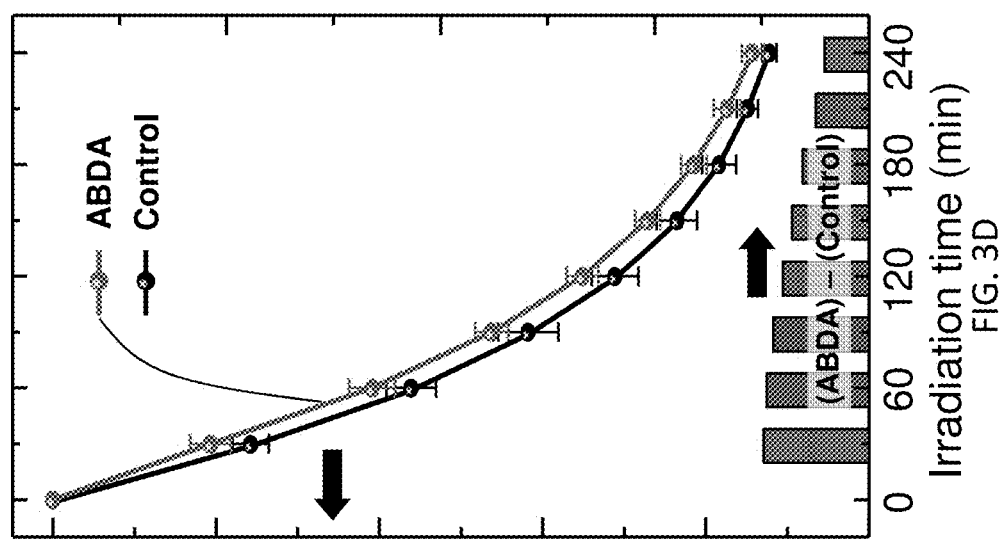
FIG. 3D is a fluorescence graph of a mixture of TEMPO-9-ac and ABDA.
Figure 3E:
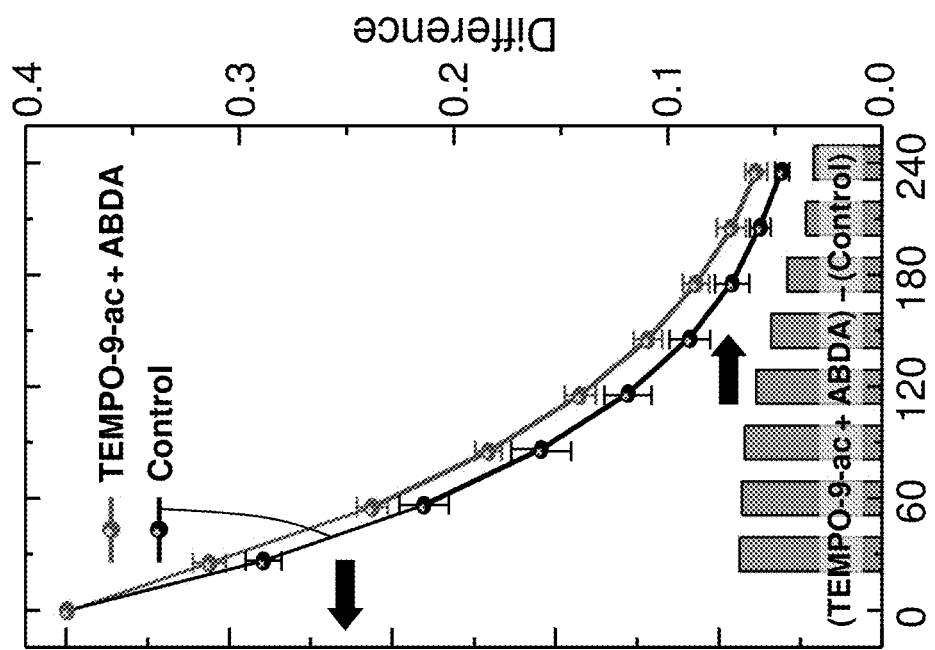
FIG. 3E a fluorescence graph that shows differences in fluorescent signals with respect to controls without the scavengers.

Specific types of ROS (e.g. $O_2^{\cdot-}$ and $^1O_2$) produced by mKate2 silk upon green light activation ($\lambda_{ex}$=532 nm and optical intensity≈0.2 mW/mm$^2$) were considered. Referring to FIGS. 3A-3E, graphs of arbitrary units (a.u.) for turn-on/off fluorescence and fluorogenic scavenger detections of ROS generated by mKate2 silk upon green light activation are presented. Fluorescent emission signals of radical sensing probes were recorded from solutions containing mKate2 silk discs. FIG. 3A shows a graph of fluorescence of $O_2^{\cdot-}$ mediated by Type I photosensitization reaction, captured by turn-on fluorescent signals of TEMPO-9-ac. FIG. 3B shows a fluorescence graph in which $O_2$ mediated by Type II photosensitization reaction is detected by reduction of the original 9,10-Anthracenediyl-bis(methylene)dimalonic acid (ABDA) fluorescence. The inset shows difference in fluorescent spectra with respect to controls before green light activation. FIGS. 3C-3E show fluorescence graphs that show reduction in photobleaching of mKate2 silk discs which is quantified by the normalized fluorescent intensity of mKate2 silk in the presence of fluorogenic scavengers of TEMPO-9-ac for $O_2$. In particular, FIG. 3C shows fluorescence for ABDA for $O_2$; FIG. 3D shows fluorescence of a mixture of TEMPO-9-ac and ABDA; and FIG. 3E shows differences in fluorescent signals with respect to controls without the scavengers.

First, $O_2^{\cdot-}$ generated by mKate2 silk via primarily Type I reaction was detected. The generation and release of $O_2^{\cdot-}$ are monitored using fluorescent sensing probes; TEMPO-9-ac is used to sense $O_2^{\cdot-}$. Under consistent green light irradiation on mKate2 silk discs immersed in TEMPO-9-ac solutions, fluorescent signals of TEMPO-9-ac ($\lambda_{ex}$≈360 nm and $\lambda_{em} \approx 440$ nm) are detected in two different configurations: i) The turn-on fluorescent probes are diffused into the TEMPO-9-ac solution.

Figure 14:
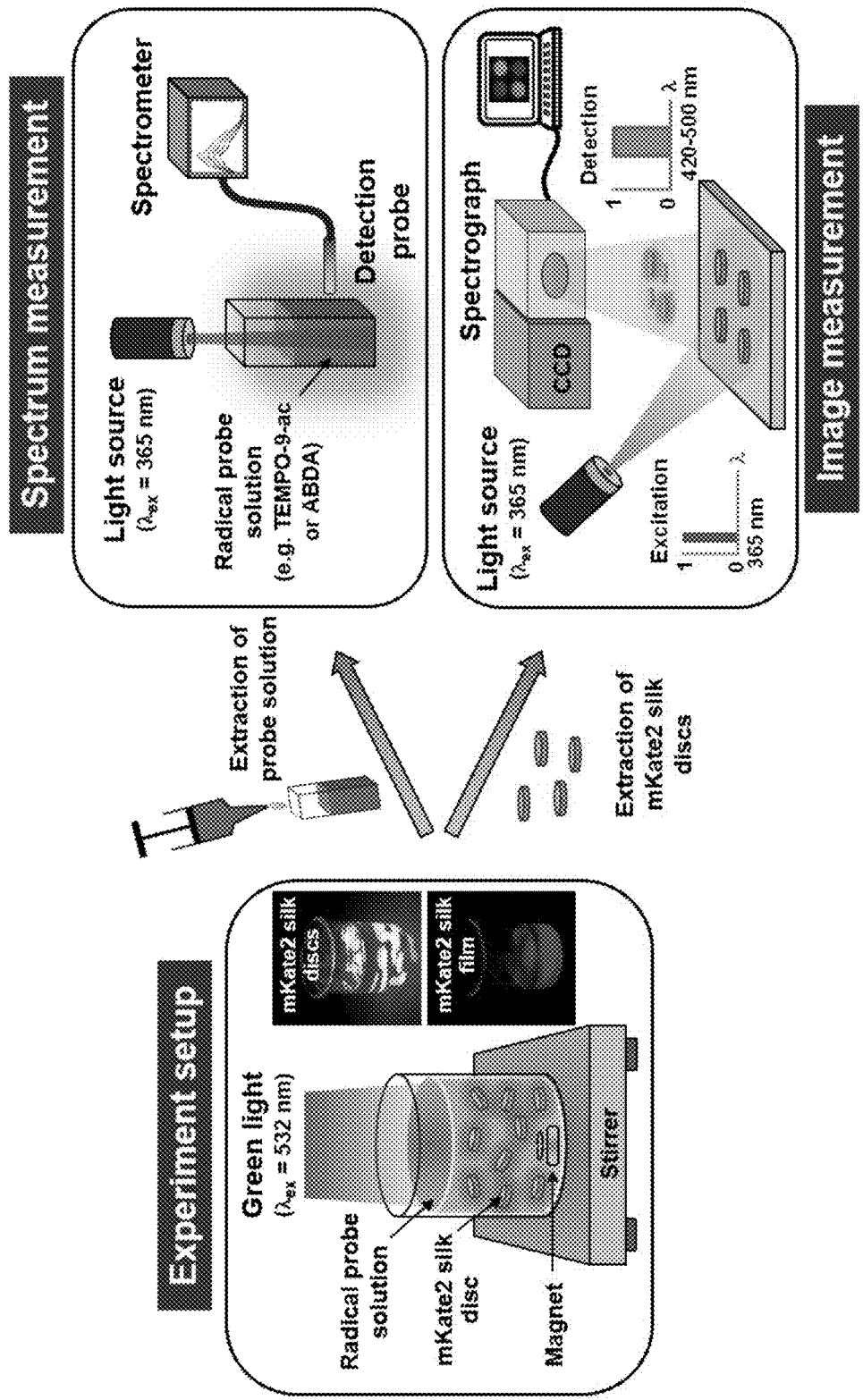
FIG. 14 are schematics of two detection scenarios for assessing ROS generated from mKate2 silk upon green light activation.

Referring to FIG. 14, two detection scenarios for assessing ROS generated from mKate2 silk upon green light activation are presented. First, spectral measurements is shown where fluorescent signals of radical probes under excitation of $\lambda_{ex} = 365$ nm are detected from the solution including mKate2 silk discs. Second, imaging measurements is shown with fluorescent radical molecular probes are permeated into mKate2 silk discs. Specimens are arranged within the field of view of the mesoscopic imaging setup, in which the excitation ($\lambda_{ex} = 365$ nm) and emission filters ($\lambda_{em} = 420\text{-}500$ nm) are used as illustrated.

Figure 15A:
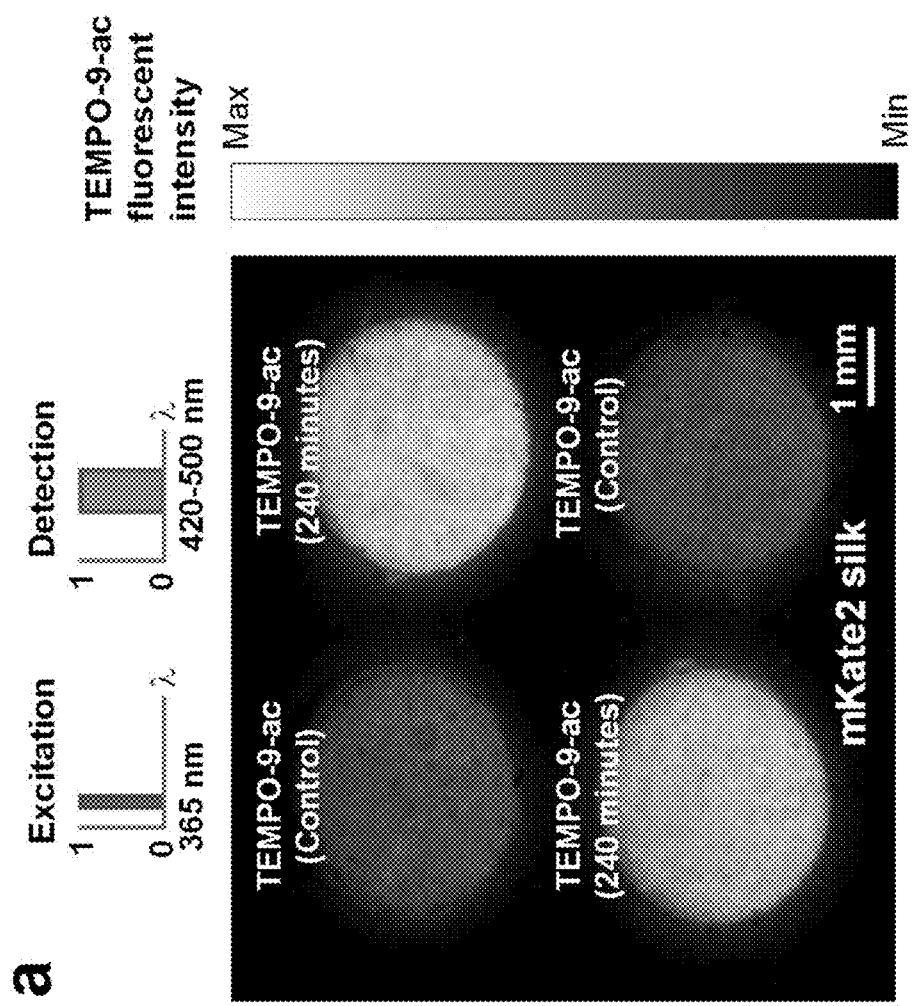
FIG. 15A is a set of fluorescent images of TEMPO-9-ac in mKate2 silk discs before (control) and after green light activation for 240 minutes.
Figure 15B:
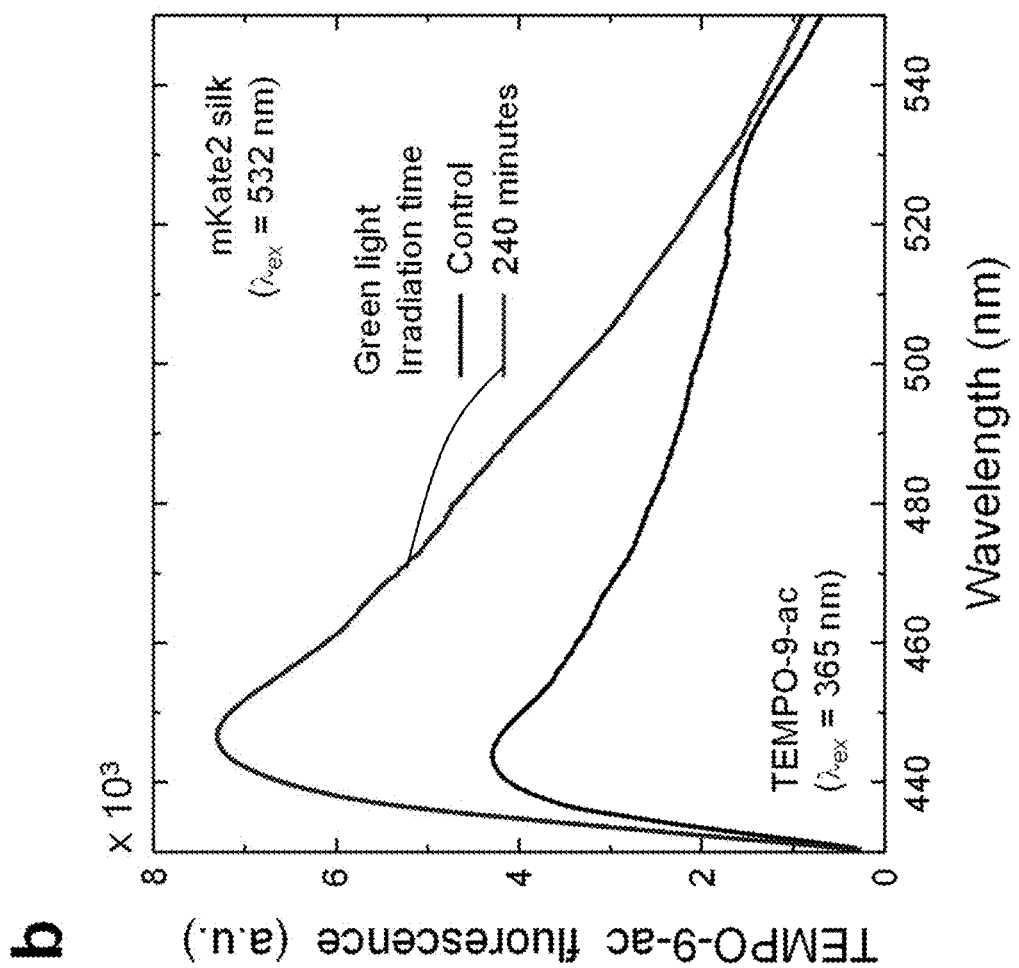
FIG. 15B is a set of fluorescent spectra of TEMPO-9-ac in mKate2 silk discs before (control) and after green light activation for 240 minutes.

Referring back to FIG. 3A, the fluorescent emission intensity of TEMPO-9-ac increases monotonously with the duration of green light irradiation, compared to the baseline signals before light activation (controls). After TEMPO-9-ac is permeated into the silk discs, the turn-on fluorescent probes remain inside, which in turn emit blue emission (i.e. fluorescent signal of TEMPO-9-ac) from the mKate2 silk discs. 240-min irradiation of green light leads to a 2-fold increase in the probe fluorescent intensity from the silk discs infiltrated with TEMPO-9-ac, compared with the unirradiated mKate2 silk discs (controls) as shown in FIGS. 15A and 15B. Referring to FIGS. 15A and 15B, turn-on fluorescent signals of TEMPO-9-ac in mKate2 silk before and after green light activation is shown. In particular, FIG. 15A shows a fluorescent image of TEMPO-9-ac in mKate2 silk discs before (control) and after green light activation for 240 minutes, while FIG. 15B shows fluorescent spectra of TEMPO-9-ac in mKate2 silk discs before (control) and after green light activation for 240 minutes.

These results are in excellent agreement with $O_2^{\cdot-}$ released from KillerRed, which is one of the highly phototoxic RFP variants. Second, we detect $^1O_2$ generated by mKate2 silk under the same green light activation via Type II reaction, using ABDA as a radical sensing probe. While the original state of ABDA emits fluorescence ($\lambda_{ex} \approx 380$ nm and $\lambda_{em} \approx 431$ nm), ABDA reacts with $^1O_2$ to yield endoperoxide as a turn-off fluorescent radial probe, thus reducing its fluorescent intensity. In FIG. 3B, the intensity of ABDA fluorescent peaks gradually drops as the irradiation time increases, supporting the generation of $^1O_2$.

Figure 16:
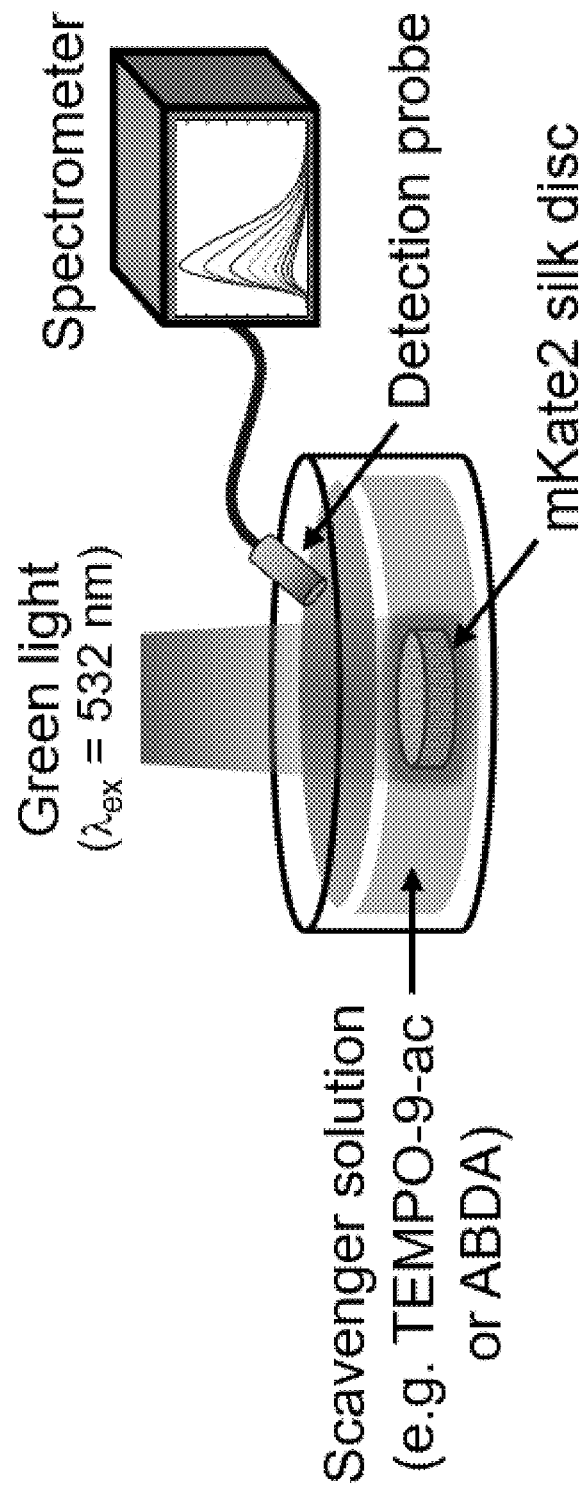
FIG. 16 is a schematic of photobleaching monitoring of mKate2 fluorescence, in accordance with the present disclosure.
Figure 17A:
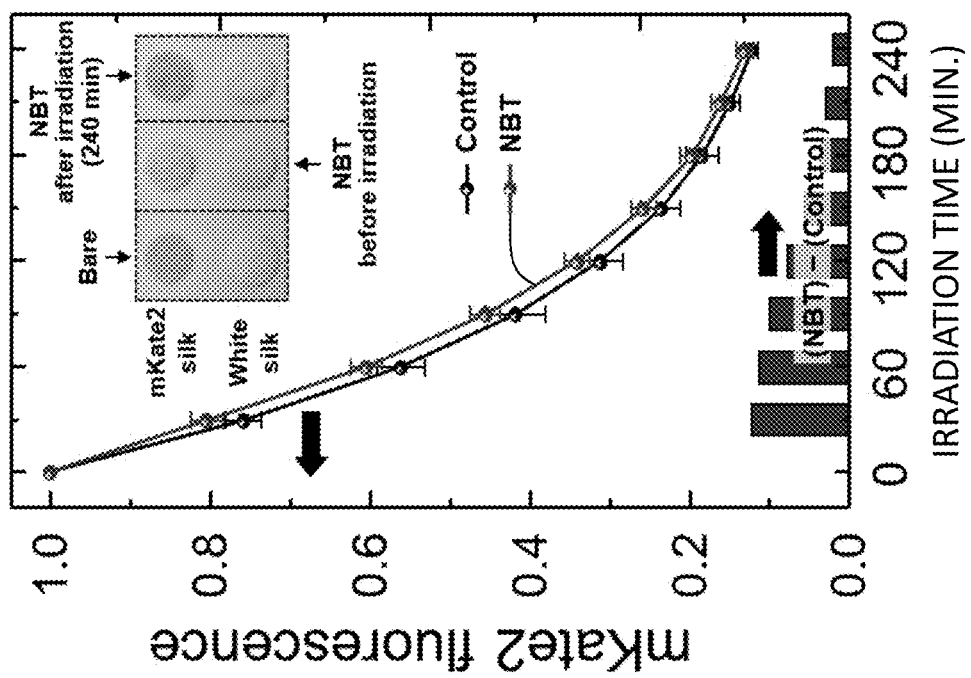
FIGS. 17A and 17B are normalized fluorescent intensity of mKate2 silk with and without scavengers of nitro blue tetrazolium chloride (NBT) for $O_2^{\cdot-}$ and sodium azide (NaN$_3$) for $^1O_2$, respectively.
Figure 17B:
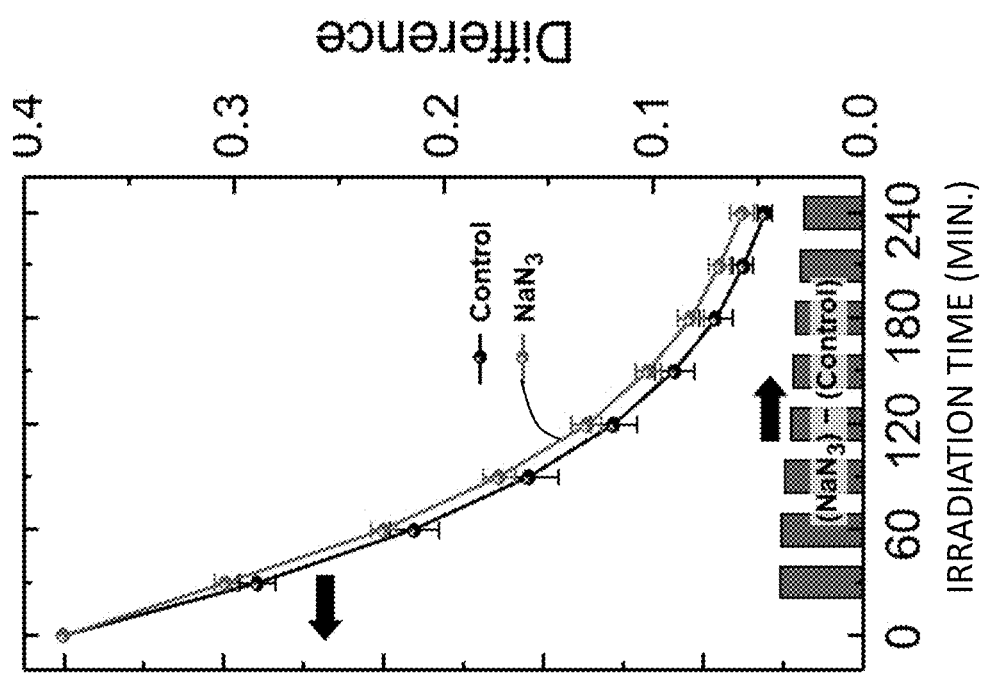

Using fluorogenic scavengers, the generation of $O_2^{\cdot-}$ and $^1O_2$ from the radical-based Type I and Type II reactions of mKate2 silk were further validated. The phototoxicity of RFP is accompanied by photobleaching, because the formation of ROS itself facilitates the degradation excitation-emission cycle of RFP. Interestingly, TEMPO-9-ac and ABDA, which are radical sensing probes, can also be used as physical quenchers of $O_2^{\cdot-}$ and $^1O_2$, respectively, without directly reacting with other free radicals. Referring to FIG. 16, photobleaching monitoring of mKate2 fluorescence is depicted, in accordance with the present disclosure. TEMPO-9-ac and ABDA, which are used as physical scavengers of ROS generated by mKate2 silk, slow down photobleaching of mKate2 in silk from phototoxic ROS. In FIGS. 3C and 3D, the inhibition of TEMPO-9-ac and ABDA in photobleaching of mKate2 silk provides another level of evidence in support of $O_2^{\cdot-}$ and $^1O_2$ production. In other words, the uptake of local surrounding ROS ($O_2^{\cdot-}$ and $^1O_2$) prevents mKate2 silk from being photodamaged, which is manifested by the relatively sustained fluorescent intensity of mKate2 silk. In a mixed solution of TEMPO-9-ac and ABDA, the fluorescent emission of mKate2 silk is further maintained (FIG. 3E). Reduction of photobleaching of mKate2 silk using other scavengers of $O_2^{\cdot-}$ (nitro blue tetrazolium chloride, NBT) and $^1O_2$ (sodium azide, $NaN_3$) is also confirmed with reference to FIGS. 17A and 17B. FIGS. 17A and 17B demonstrate fluorogenic scavenger detection of ROS generated by mKate2 silk upon green light activation using additional scavengers. FIGS. 17A and 17B show normalized fluorescent intensity of mKate2 silk with and without scavengers of nitro blue tetrazolium chloride (NBT) for $O_2^{\cdot-}$ and sodium azide ($NaN_3$) for $^1O_2$, respectively. Differences in fluorescent spectra with respect to controls without the scavengers are also shown. Top inset of FIG. 17A shows a photograph of bare and NBT-treated (before and after light activation) white and mKate2 silk discs, showing $O_2^{\cdot-}$ generated from mKate2 silk. After 240-min green light irradiation, there are no variations in the color (yellow) of white silk, while mKate2 silk changes to the bluish color, resulting from the formation of blue chromagen diformazan. The error bars are standard deviations.

Figure 18A:
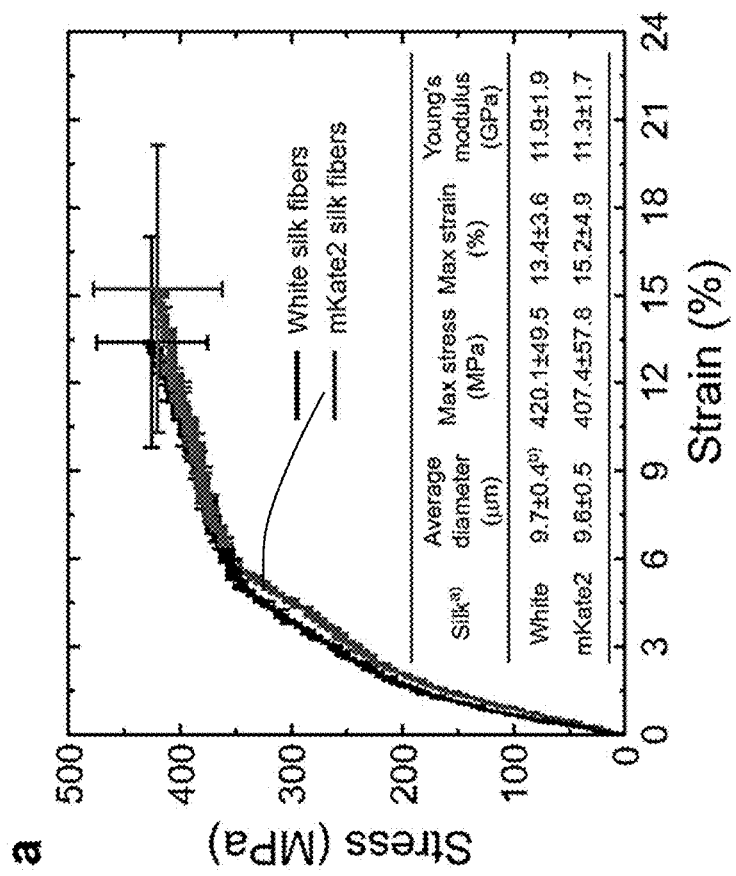
FIG. 18A is a strain-stress curve of white and mKate2 silk fibers. The error bars are standard deviations in elongation at break (horizontal axis) and fracture strength (vertical axis).
Figure 18B:
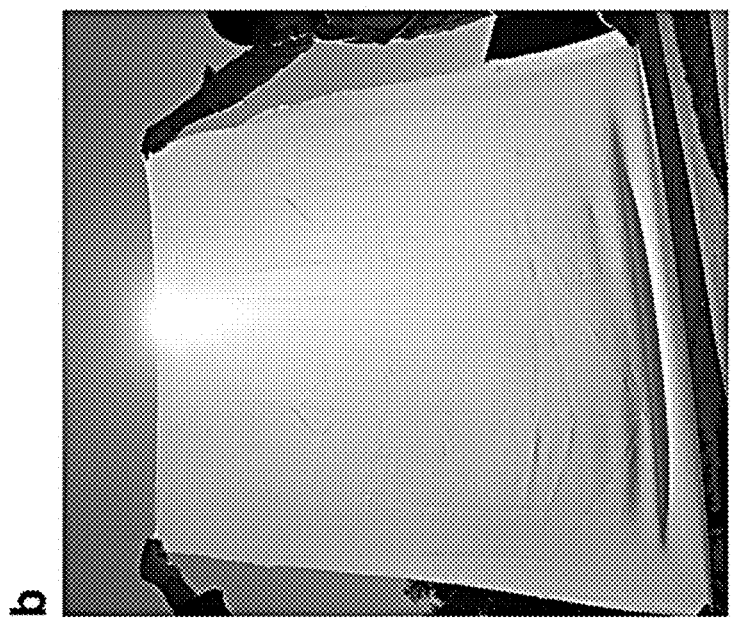
FIG. 18B is a photograph of a woven silk fabric of about 110 cm×140 cm.

The direct use of silk fibers produced by silkworms has its own advantage as used in the textile industry, because the transgenic silk has comparable mechanical properties to make woven fabrics, as shown in FIGS. 18A and 18B. Referring to FIGS. 18A and 18B, results of mechanical tests of mKate2 silk and scalability/continuous manufacturing of silk fabrics are shown. FIG. 18A provides representative strain-stress curves of white and mKate2 silk fibers. The error bars are standard deviations in elongation at break (horizontal axis) and fracture strength (vertical axis). For each silk type, at least 10 randomly selected single fibers of three silk cocoons are tested for statistical analysis. The Young's moduli are calculated from the first linear regime of the strain-stress curve before the first bend. FIG. 18B shows a photograph of 110 cm×140 cm silk fabric woven. This white silk fabric did not undergo any additional chemical treatments except for degumming (i.e. sericin removal), showing the possibility of scalable and continuous production using the conventional textile infrastructures. To evaluate the basic mechanical property (i.e. strain-stress curves) of mKate2 silk fibers, a universal electromechanical test machine 100P/Q (TestResources Inc.) was used at an extension rate of 1 mm/min and a gauge length of 10 mm under ambient conditions. For both white and mKate2 silk fibers, at least 10 randomly selected single fibers from three different cocoons were tested. As shown in FIG. 18A, mKate2 silk fibers exhibit no considerable change in the mechanical properties, such as the maximum strain, the maximum stress, and the Young's modulus (p-value=0.4). Thus, mKate2 silk fibers can be treated as conventional silk fibers that are woven or constructed into large-area and continuous fabrics using the textile technologies (e.g. knitted dresses and suits) as shown in FIG. 18B. In other words, mKate2 silk could easily be woven or constructed into large-area and continuous fabrics using the existing textile infrastructure in a scalable manner.

Figure 4A:
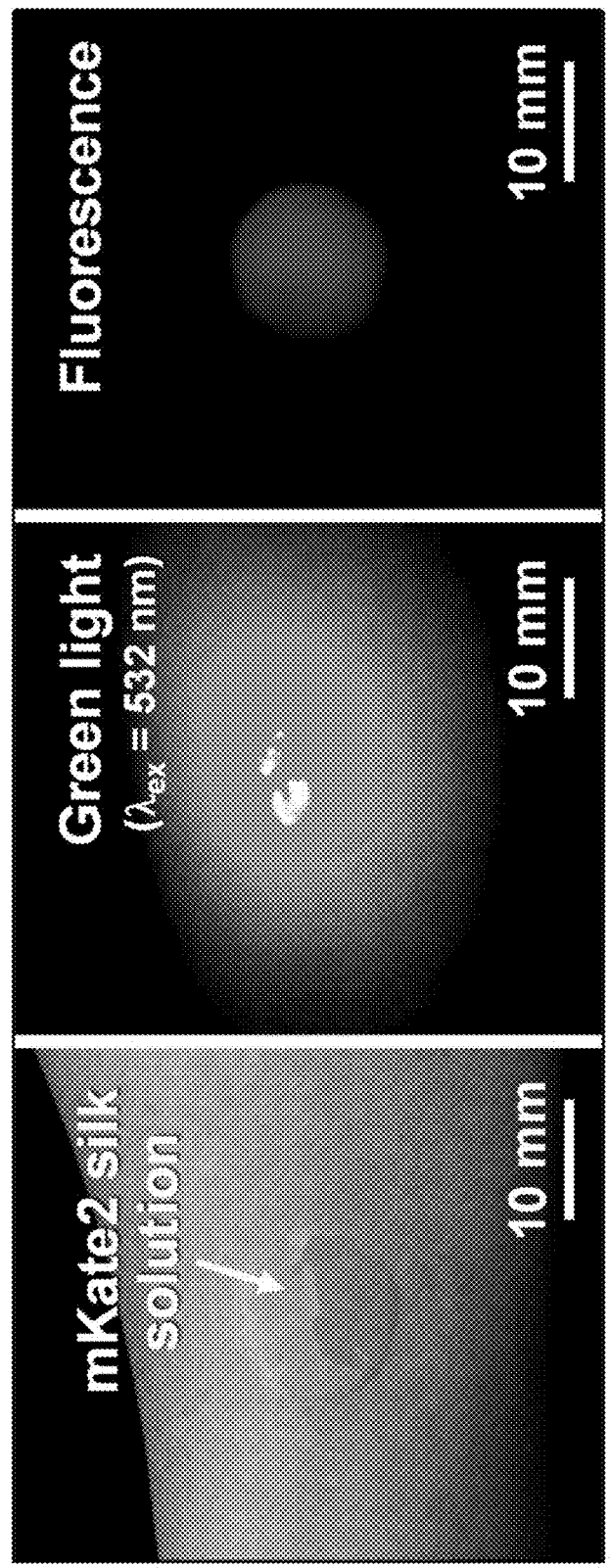
FIG. 4A is a set of photographs and fluorescent images of mKate2 silk solution and film.
Figure 4B:
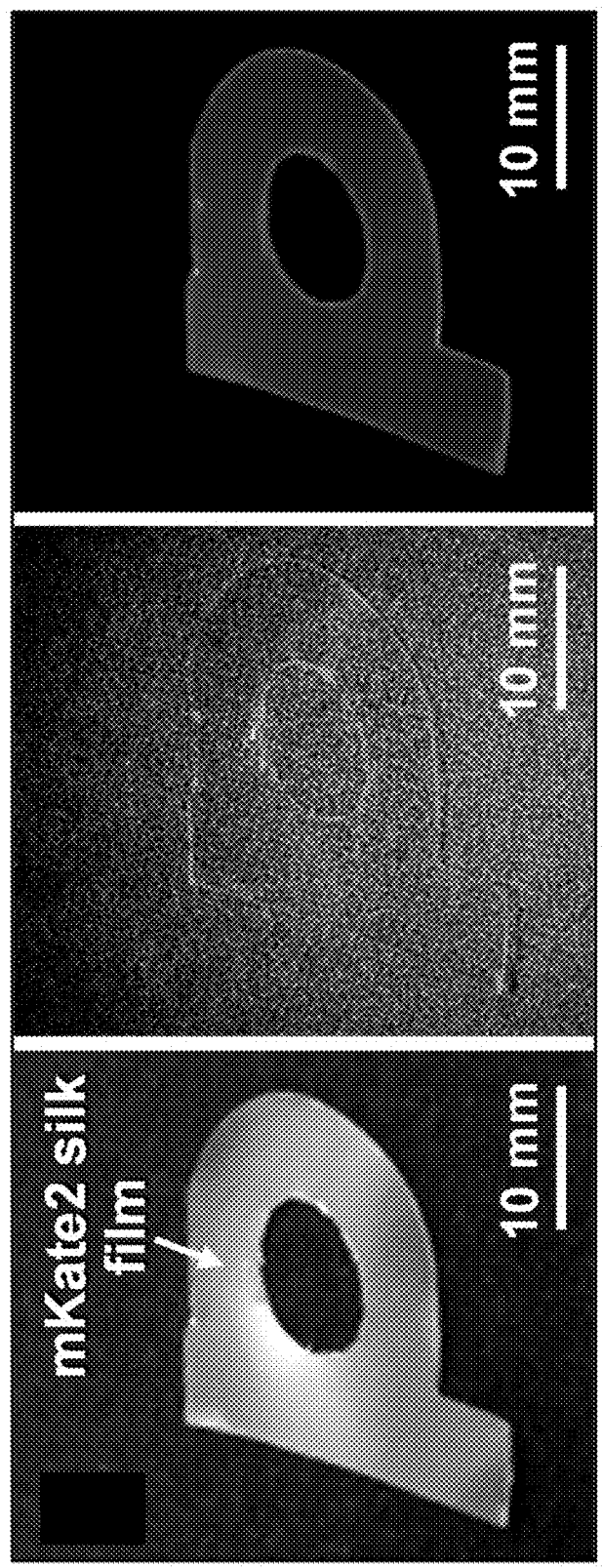
FIG. 4B is another set of photographs and fluorescent images of mKate2 silk solution and film.
Figure 4C:
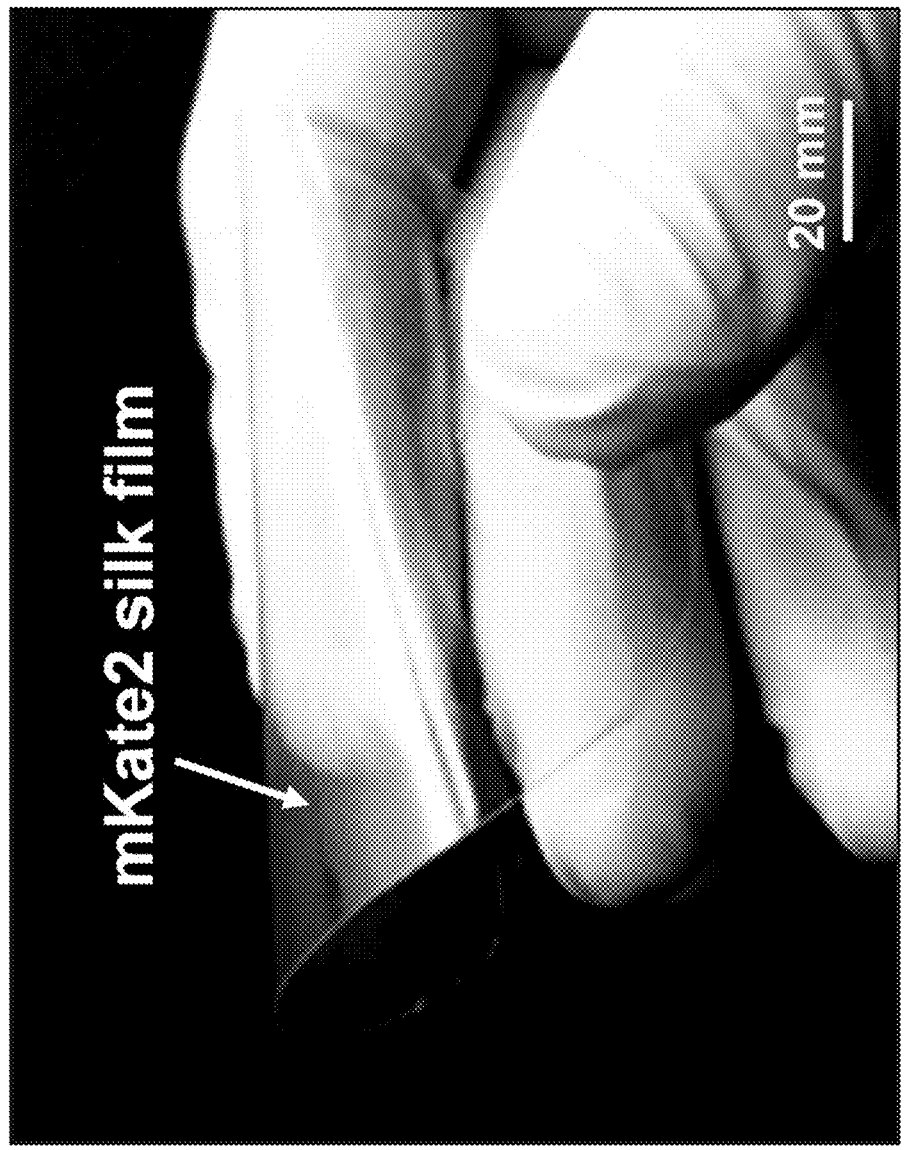
FIG. 4C is a photograph of large-area flexible mKate2 silk film with a diameter of about 120 mm.
Figure 4D:
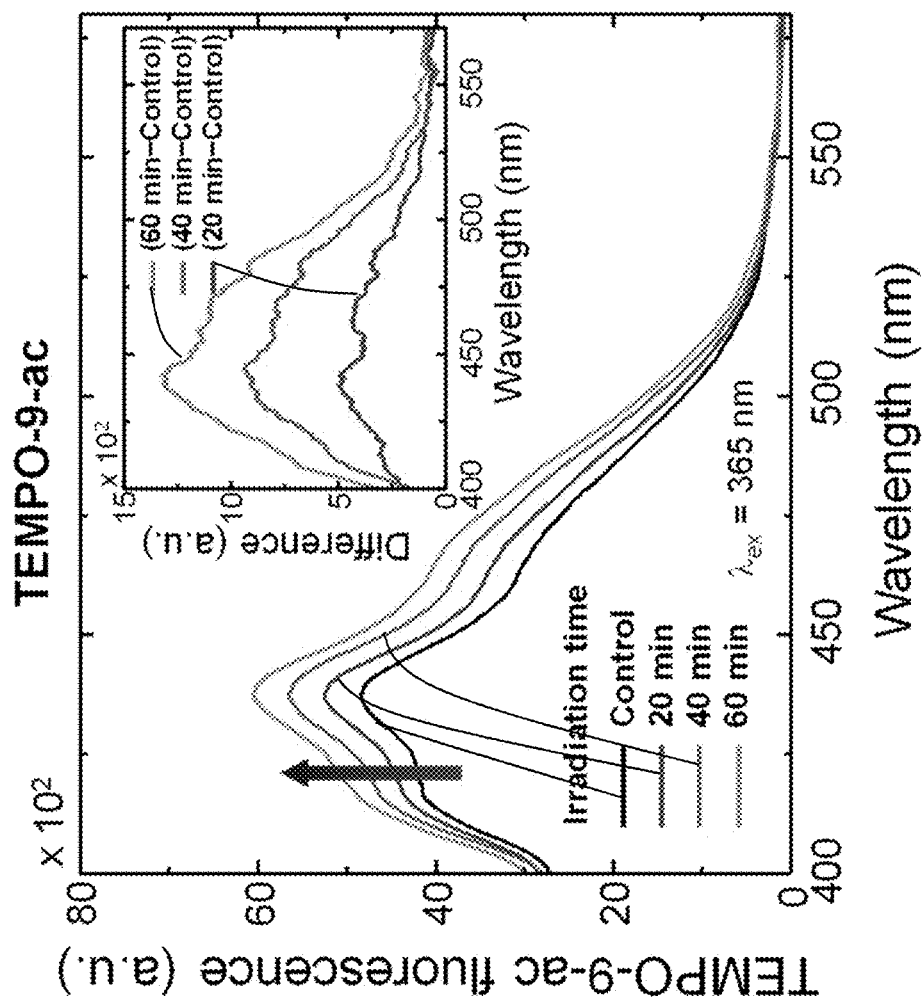
FIG. 4D is a graph of fluorescent emission signals of radical sensing probes of TEMPO-9-ac for $O_2^{\cdot-}$. The inset of FIG. 4D shows differences in fluorescent spectra with respect to controls (before green light activation).
Figure 4E:
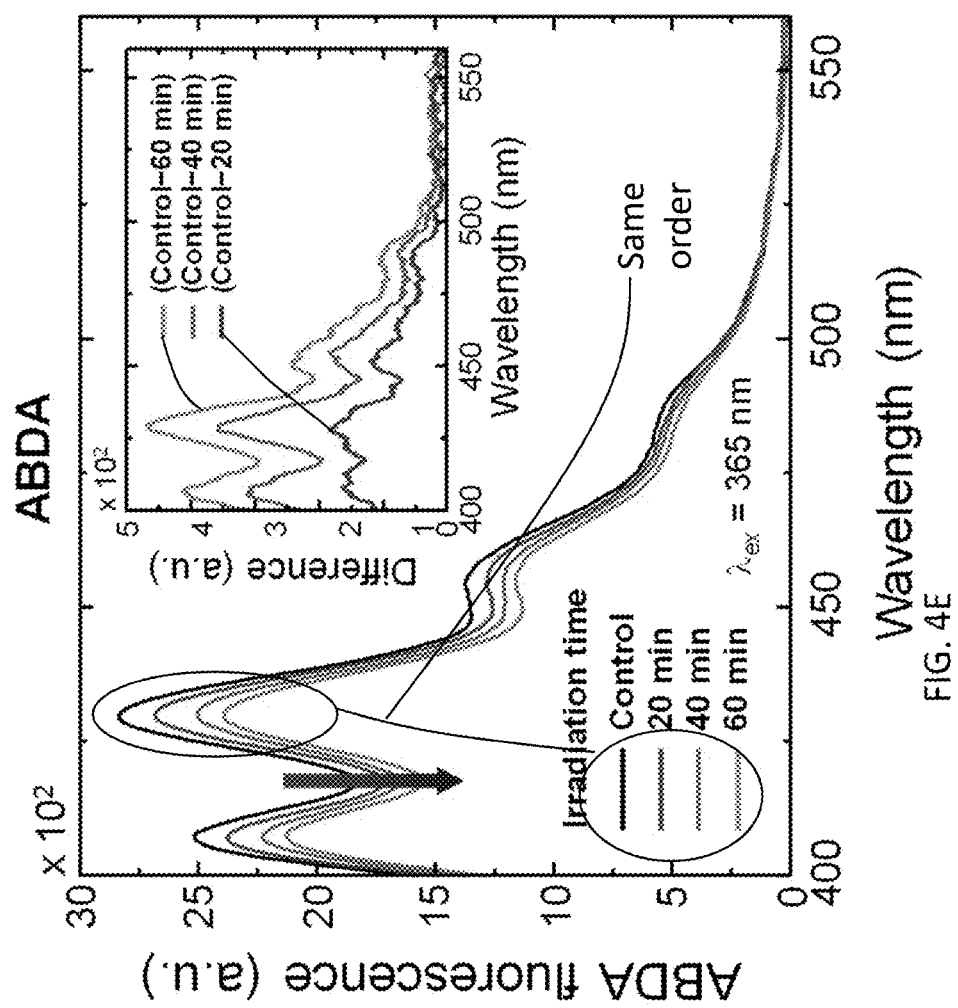
FIG. 4E is a graph of fluorescent emission signals of radical sensing probes of TEMPO-9-ac for ABDA. The inset of FIG. 4E shows differences in fluorescent spectra with respect to controls (before green light activation).
Figure 6A:
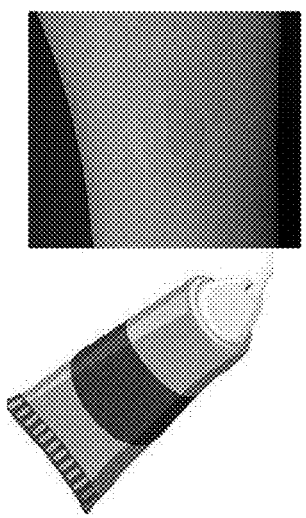
FIGS. 6A-6D are schematics of various other embodiments of fluorescent silk polymers including an ointment gel for wounds to be applied directly to skin surface, polymer films, mask packs, and separate bandage patches attachable to existing bandages.
Figure 6B:
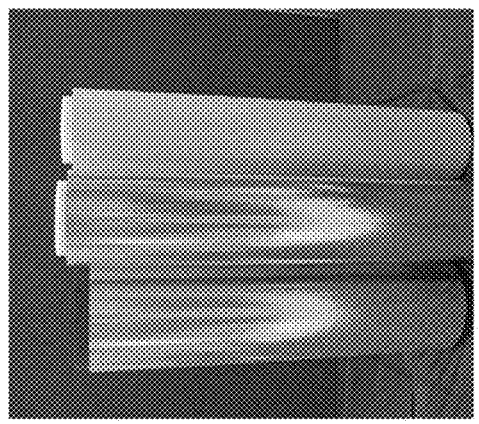
Figure 6C:
Figure 6D:
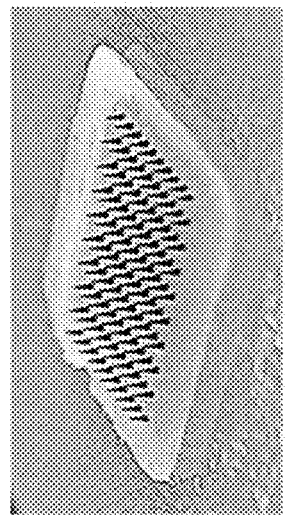
Figures 19A, 19B:
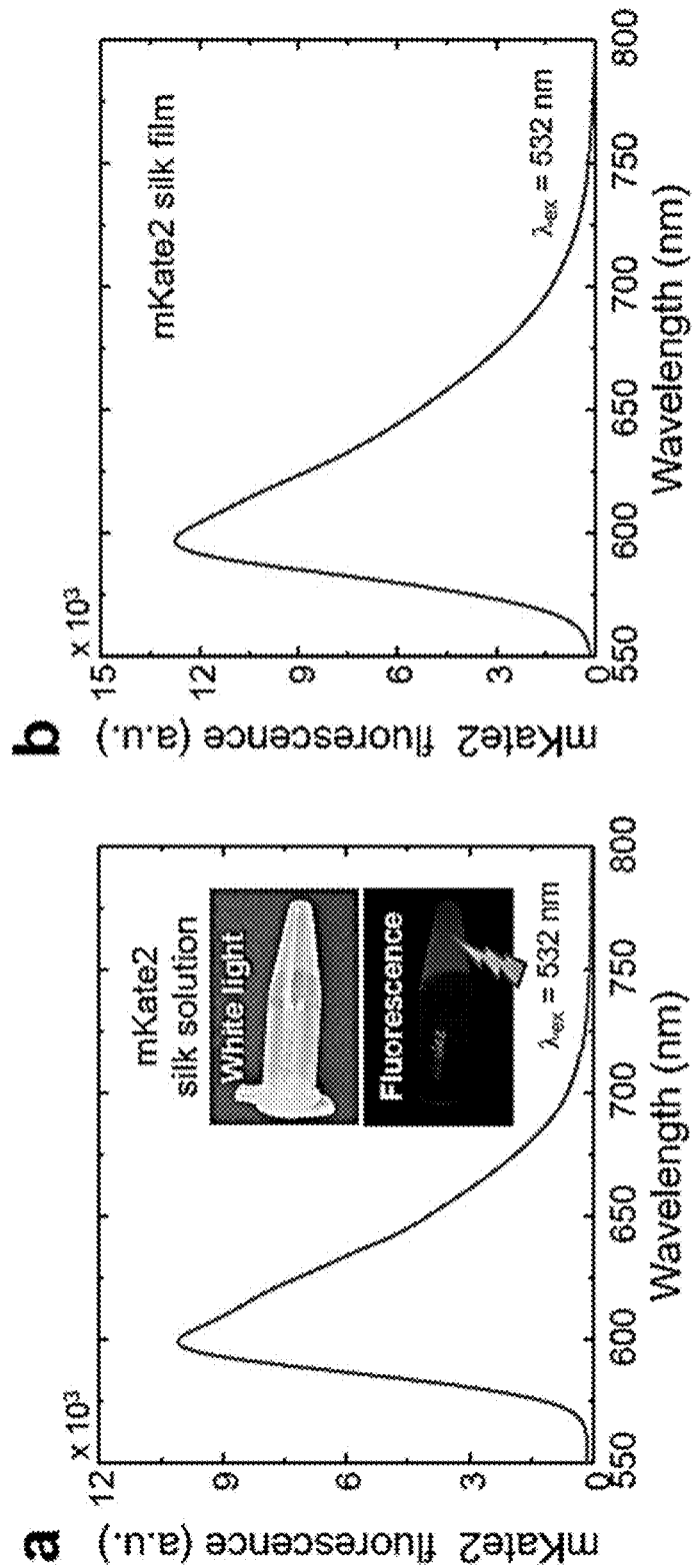
FIGS. 19A and 19B are fluorescent spectra of regenerated mKate2 silk in forms of a solution (FIG. 19A) and a film (FIG. 19B), respectively.
Figure 19C:
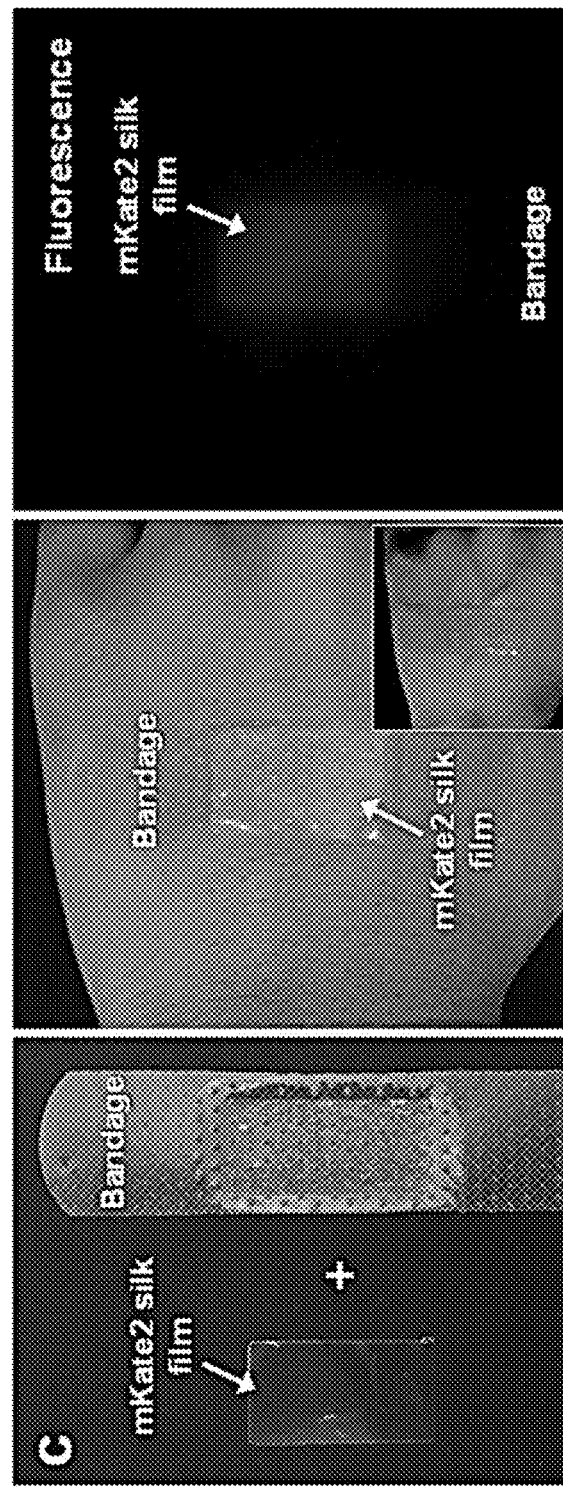
FIG. 19C is a schematic showing capability of a regenerated mKate2 silk film to be integrated with a bandage, offering an additional functionality of controllable ROS release using a simple light source.
Figures 20A, 20B:
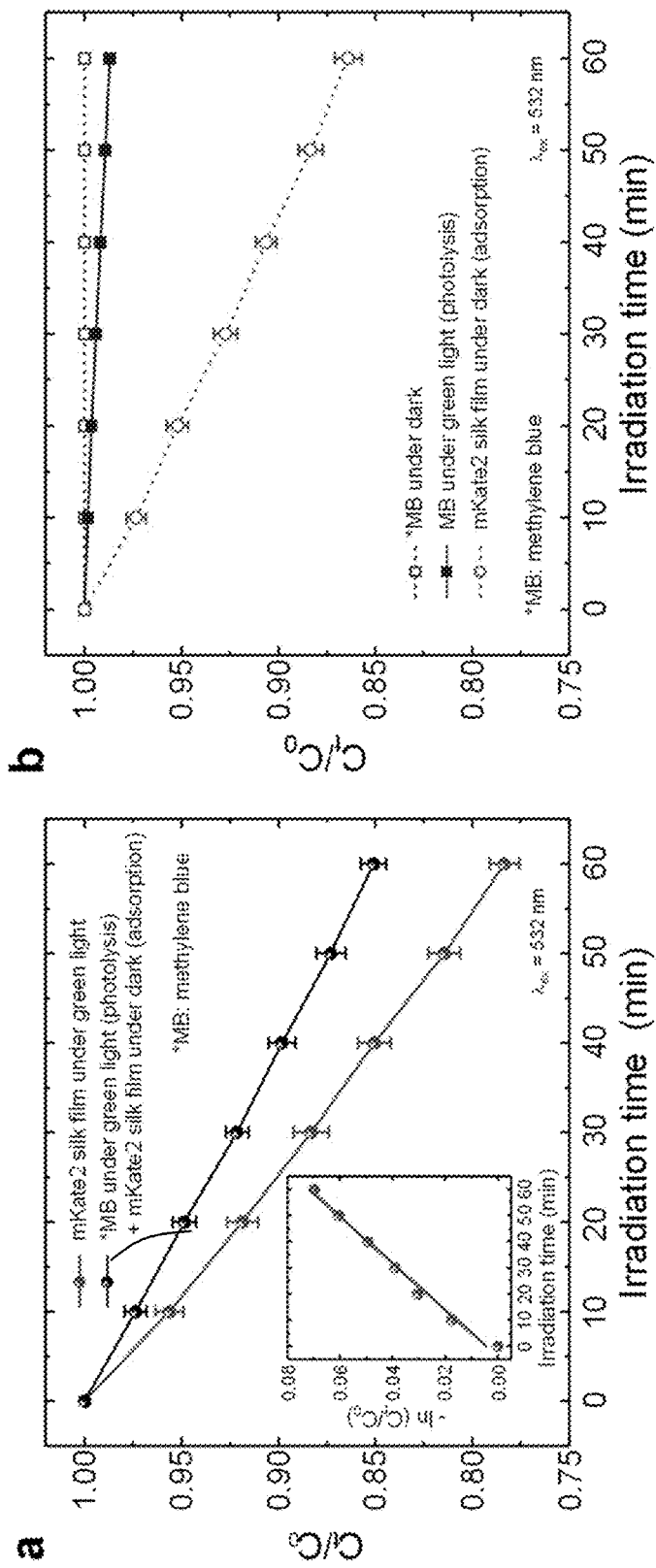
FIG. 20A is a graph of $C_t/C_0$ vs. irradiation time (in min) showing photodegradation of methylene blue upon green light activation is shown. The inset of FIG. 20A shows a kinetic plot for methylene blue degradation by mKate2 silk film after factoring out the adsorbent effect of mKate2 silk film and the photolytic effect of light irradiation (kapp=1.12×10−3 min-1).
FIG. 20B is a graph of $C_t/C_0$ vs. irradiation time (in min) showing confounding factors in photodegradation of methylene blue by mKate2 silk film for the adsorption of methylene blue to the mKate2 silk film and the photolysis of methylene blue under the green light irradiation are provided. The error bars represent standard deviations.

Silk fibroin can further be processed into polymeric materials for fabricating artificially engineered biomaterials and optical materials in a variety of forms with biocompatibility and bioabsorbablity. However, the conventional fibroin extraction methods are inappropriate for mKate2 silk, because fluorescent proteins are highly susceptible to denaturation from high temperature and pH values. Minimizing heat-induced denaturation of mKate2, we process mKate2 silk fibroin to an aqueous solution and then form a flexible thin film (FIGS. 4A, 4B, and 4C). Referring to FIGS. 4A-4C, regenerated mKate2 silk and detection of ROS generation upon green light activation is shown. Fluorescent emission signals of radical sensing probes are recorded from regenerated mKate2 silk solutions and films. With reference to FIGS. 4A and 4B, photographs and fluorescent images of mKate2 silk solution and film are shown. With reference to FIG. 4C, a photograph of large-area flexible mKate2 silk film with a diameter of 120 mm is shown. With reference to FIGS. 4D and 4E, fluorescent emission signals of radical sensing probes of TEMPO-9-ac are provided, for $O_2^{\cdot-}$, as shown in FIG. 4D, and for ABDA for $^1O_2$ as shown in FIG. 4E. Insets of FIGS. 4D and 4E show differences in fluorescent spectra with respect to controls (before green light activation). The red fluorescent emission is maintained in both the regenerated mKate2 silk solution and film under green light excitation as depicted in FIGS. 19A and 19B. With reference to FIGS. 19A and 19B, fluorescent spectra of regenerated mKate2 silk and representative utilization of regenerated mKate2 silk are shown, in forms of a solution (FIG. 19A) and a film (FIG. 19B), respectively. Inset of FIG. 19A shows a photograph and fluorescent image of the mKate2 silk solution. With reference to FIG. 19C, capability of a regenerated mKate2 silk film is shown to be integrated with a bandage, offering an additional functionality of controllable ROS release using a simple light source. The generation of $O_2^{\cdot-}$ and $^1O_2$ from the regenerated mKate2 silk products is also detected using TEMPO-9-ac and ABDA, respectively (see FIGS. 4D and 4E). With the prolonged green light irradiation ($\lambda_{ex}$=532 nm and optical intensity≈0.2 mW/mm$^2$), the fluorescent signal of TEMPO-9-ac increases, while that of ABDA decreases, supporting the two types of ROS generation, respectively. Similarly, the photodegradation of methylene blue in the mKate2 silk film results in $k_{app}$=1.12×10$^{-3}$ min$^{-1}$ under green light irradiation, after removing the confounding effects (i.e. adsorption of methylene blue to silk and photolysis of methylene blue due to green light irradiation) as shown in FIGS. 20A and 20B. The photodegradation of methylene blue from mKate2 silk films under the green light activation ($\lambda_{ex}$=532 nm and optical intensity≈0.2 mW/mm2) was thus validated. With reference to FIGS. 20A and 20B, photocatalytic activity of regenerated mKate2 silk for degrading methylene blue under green light activation at the ambient temperature is depicted. In particular, with reference to FIG. 20A, photodegradation of methylene blue upon green light activation is shown. The inset of FIG. 20A shows a kinetic plot for methylene blue degradation by mKate2 silk film after factoring out the adsorbent effect of mKate2 silk film and the photolytic effect of light irradiation (kapp=1.12×10−3 min−1). With reference to FIG. 20B, confounding factors in photodegradation of methylene blue by mKate2 silk film for the adsorption of methylene blue to the mKate2 silk film and the photolysis of methylene blue under the green light irradiation are provided. The error bars represent standard deviations.

Various embodiments representing applications of mKate2 silk or other variations of the genetically modified silkworm produced silk is shown in FIGS. 5A-5E. These applications include protective suits including scrubs, gloves, or other sheet material that can be used in medical and non-medical garment industry (including for burn patients), masks, wallpaper, bandages, and filtration applications (water, air, and other filters known to a person having ordinary skill in the art).

Various other embodiments of fluorescent silk polymers are shown IN FIGS. 6A-6D, which include an ointment gel for wounds to be applied directly to skin surface, polymer films, mask packs, and separate bandage patches attachable to existing bandages.

Figure 7:
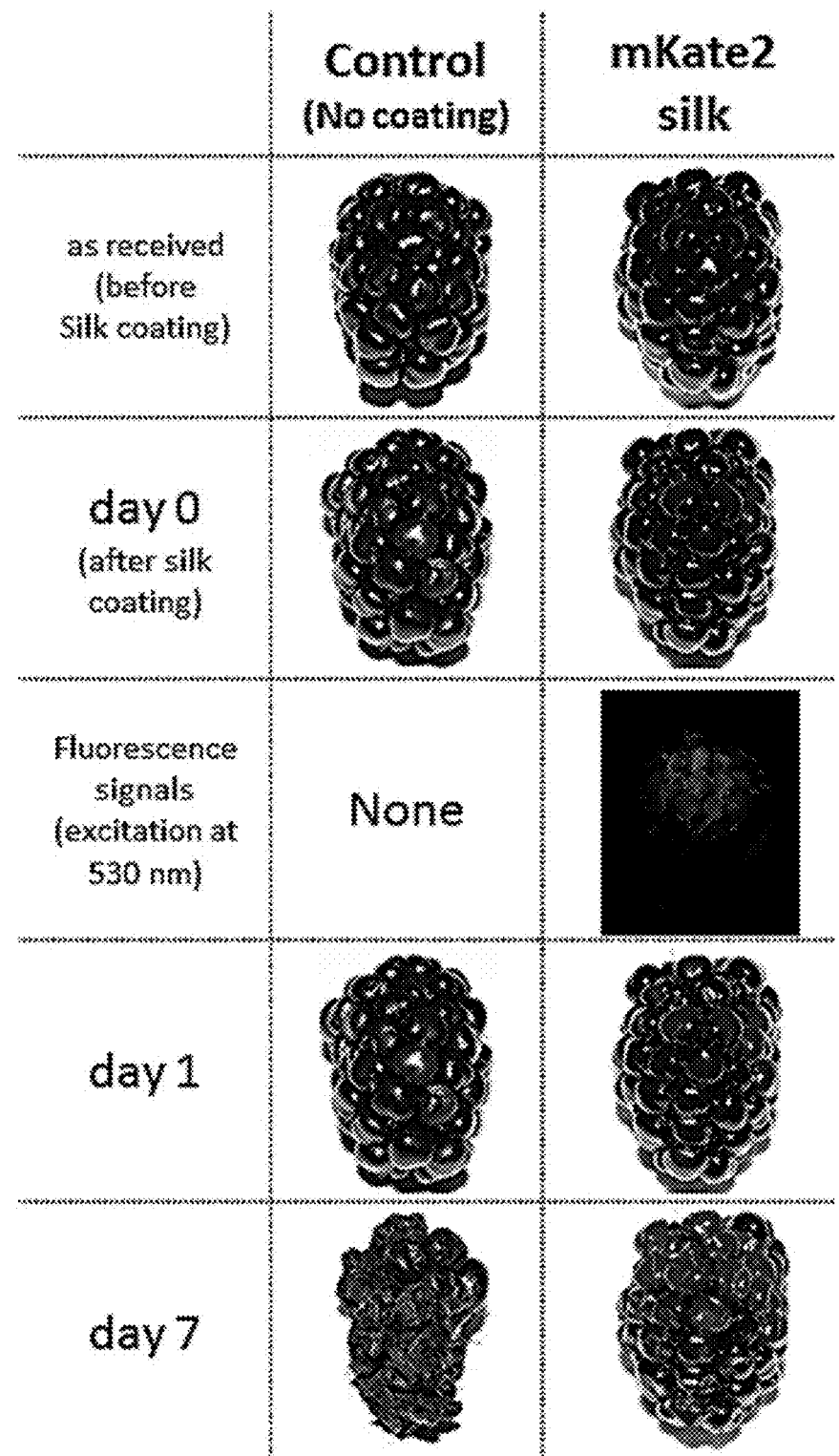
FIG. 7 is a set of photographs of blackberry fruit which is wrapped with mKate2 silk, for day 1 and day 7, as compared to a control population which is free of mKate2.

In another embodiment, given the edible nature of mKate2 silk, fruits can be wrapped with the material to preserve for longer periods of time. Referring to FIG. 7, blackberry fruit is wrapped with mKate2 silk, and as shown in day 7, while a control population is degraded significantly, the fruit wrapped with mKate2 silk remains substantially unchanged.

Figure 8:
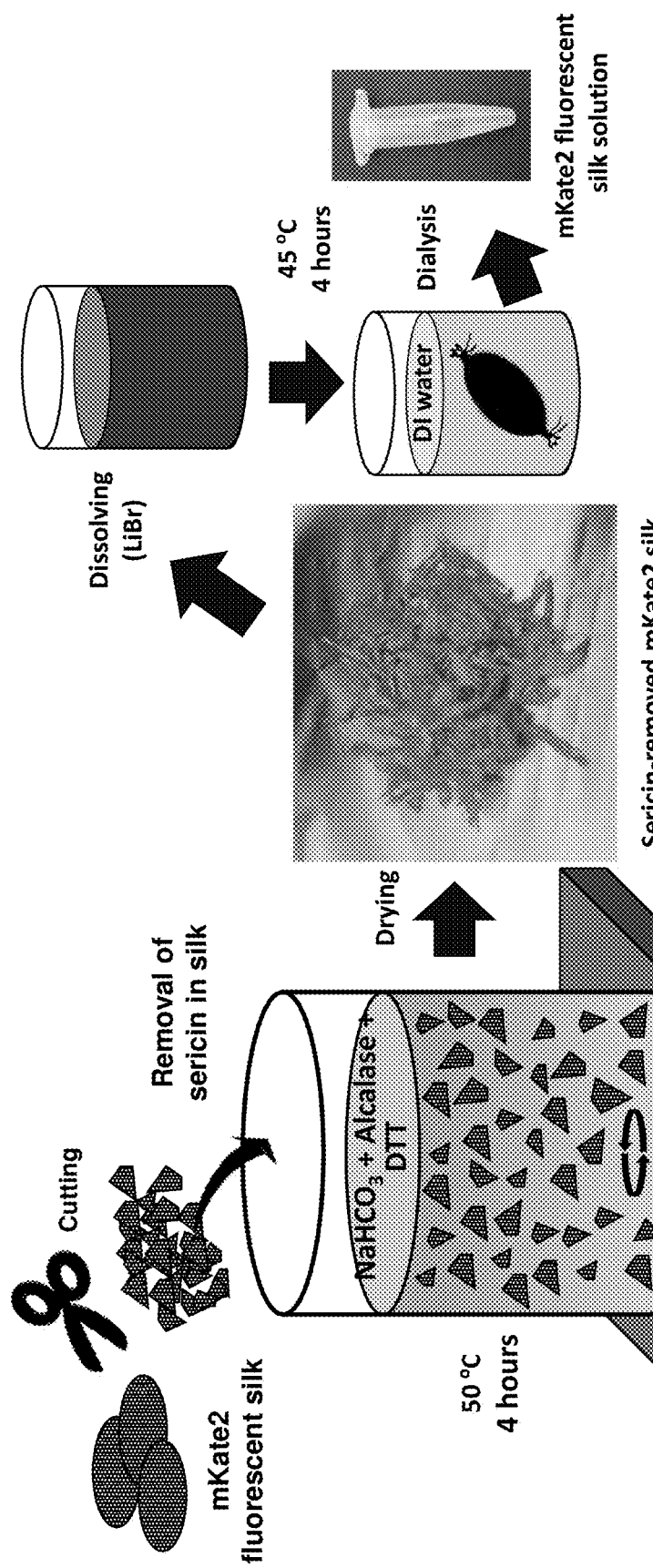
FIG. 8 is a schematic of a process for making various embodiments of mKate2 silk.

Referring to FIG. 8, a process for making various embodiments of mKate2 silk is shown. The process includes, harvesting mKate2 silk, cutting the material into small pieces, placing the cut material into a solution to remove sericin in the silk. In the embodiment shown NaHCO$_3$+ Alcalase+dithiothreitol (DTT) is used as the solvent for about 4 hours at about 50° C., but other solvents and processes known to a person having ordinary skill can be used. Once the sericin has been removed from the cut pieces, sericin-removed mKate2 silk is substantially dried and then dissolved in a solution (LiBr) for 4 hours at 45° C. The dissolved mKate2 silk is then taken through a dialysis process by placing it in DI water to generate mKate2 fluorescent silk solution.

The results show that one purpose of fluorescent proteins existing in nature could be photoinducible ROS generation, while the fluorescent emission may be a secondary consequence. Specifically, ROS generation from fluorescent proteins involves long-range electron transfer via two possible mechanisms of direct tunneling and hopping inside fluorescent proteins. The current understanding of this process is based on quantum mechanics, because electron tunneling over such a long distance of 1.5-3 nm is typically impossible in vacuum. As an electron donor, (E)GFP has been successfully tested for generating electricity as photovoltaics for bioenergy applications. However, we note that the direct photosensitization properties of RFP have not yet been exploited for scalable photocatalysis.

While mKate2 silk is discussed primarily in the present disclosure, other fluorescent transgenic silk can replace mKate2 silk in each embodiment. These include KillerRed, SuperNova, KillerOrange, Dronpa, TurboGFP, and mCherry, which all have similar a β-barrel structure with a water-filled pore, and which can also be used to tune the excitation wavelength range and to select the photosensitization properties.

Experimental Section

Materials: For silkworm transgenesis for producing mKate2 silk, we used *Bombyx mori* bivoltine strain, Keumokjam (F1 hybrid between the Japanese parental line Jam 125 and the Chinese parental line Jam 140) from the National Academy of Agricultural Science (Wanju, South Korea). DNA-injected eggs were kept at 25° C. in moist Petri dishes. The hatched larvae (i.e. silkworms) were reared in groups and fed with mulberry leaves under standard conditions (e.g. 25±2° C. and 80±10% relative humidity). For wild-type white silk, *Bombyx mori* (Baekokjam, Jam 123×Jam 124) was used.

We used the following chemicals as received: Methylene blue ($C_{16}H_{18}ClN_3S$, 0.05 wt. % in $H_2O$), dimethyl sulfoxide (DMSO; $(CH_3)_2SO$, 99%), phosphate buffered saline (PBS; pH 7.4), sodium carbonate ($Na_2CO_3$, ≥99%), Triton X100, alcalase enzyme, dithiothreitol (DTT; $C_4H_{10}O_2S_2$, ≥98%), lithium bromide (LiBr, ≥99%), dialysis tube (pore size 12,000 Da MWCO), miracloth (pore size 22-25 μm), 9,10-anthracenediyl-bis(methylene)dimalonic acid (ABDA; $C_{22}H_{18}O_8$, ≥90%), sodium azide (NaN$_3$, ≥99.5%), and nitro blue tetrazolium chloride (NBT; $C_{40}H_{30}Cl_2N_{10}O_6$, ≥98%) were purchased from Sigma-Aldrich Co. (Milwaukee, USA). 4-[(9-acridinecarbonyl)amino]-2,2,6,6-tetramethylpiperidin-1-oxyl (TEMPO-9-ac; $C_{23}H_{26}N_3O_2$, 95%) was purchased from Synchem UG & Co. KG (Altenburg, Germany). De-ionized (DI) water (Milli-Q® system) was used in all of the experiments. All experiments were performed under the ambient conditions (22±2° C. and 40±10% relative humidity).

Construction of plasmid vector DNA for silk transgenesis: We constructed the transition vector p3xP3-EGFP-pFibH-mKate2 as the piggyBac-derived vector and injected the vector DNA with a helper vector into pre-blastoderm embryos, as shown in the construction sequence map. To obtain the fibroin pormoter, the DNA fragment (GenBank Accession No. AF226688, nucleotides 61312-63870) including pFibH promoter domain (1124 bp), N-terminal region 1 (NTR-1, 142 bp), first intron (871 bp), and N-terminal region 2 (NTR-2, 417 bp) was amplified by polymerase chain reaction (PCR) using the genomic DNA from Bombyx mori and specific primers (pFibHN-F: 5'-GGCGCGCCGTGCGTGATCAGGAAAAAT-3' and pFibHN-R: 5'-TGCACCGACTGCAGCACTAGTGCT-GAA-3'), followed by treatments with restriction enzymes of AscI/NotI. The resultant DNA fragment was cloned into pGEM-T Easy Vector System (Promega, Co), named as pGEMT-pFibH-NTR. The DNA fragment (GenBank Accession No. AF226688, nucleotides 79021-79500) including C-terminal region (179 bp, CTR) and poly(A) signal region (301 bp) of the heavy chain was amplified by PCR using genomic DNA from Bombyx mori and specific primers (pFibHC-F: 5'-CCTGCAGGAAGTCGACAGCGTCAGT-TACGGAGCTGGCAGGGGA-3' and pFibHC-R: 5'-GGCCGGCC TATAGTATTCTTAGTTGAGAAGG-CATA-3') and then the resultant DNA fragment was cloned into pGEM-T Easy Vector System with the restriction enzymes of SalI/SbfI/FseI, named as pGEMT-CTR. And then, these two fragments were cloned with pBluescriptII SK(−) (Stratagene, CA) digested with ApaI/SalI, creating pFibHNC-null. The mKate2 gene was synthesized from BIONEER Co., and then it was cloned into pGEM-T Easy Vector System pGEMT-mKate2 (720 bp). N- and C-terminal had the NotI and SbfI restriction sites, respectively. The mKate2 cDNA was digested with NotI/SbfI and subcloned into a pFibHNC-null digested with NotI/SbfI, resulting in pFibHNC-mKate2. The pFibHNC-mKate2 vector was digested with AscI/FseI and subcloned into pBac-3xP3-EGFP. The resultant vector was named as p3xP3-EGFP-FibH-mKate2.

Removal of sericin in silk—Degumming: For effective generation and release of reactive oxygen species (ROS) from mKate2 silk, it was critical to remove the outermost layer of silk fibers, which is also known as sericin. We removed sericin using a degumming process. We note that the outer sericin layer is commonly removed to improve the color, sheen, and texture of silk, in the silk textile industry. To minimize the denaturation of both silk and fluorescent proteins, mKate2 silk cocoons were soaked in a pre-warmed mixture solution of $Na_2CO_3$ (0.2%) and Triton X100 (0.1%) at a low temperature of about 60° C. under a vacuum pressure. During the degumming process, low pressure treatments of 620 mmHg were repeated several times to uniformly infiltrate the solution between silk fibers to remove most sericin. The degummed cocoons were dried at air ambient.

Irradiation sources for green light: For excitation of mKate2 silk, we used two different green light sources with different optical intensities: i) A diode-pumped solid-state laser coupled with a 10× zoom Galilean beam expander was used ($\lambda$=532 nm and optical intensity≈0.2 mW/mm² on the sample surface). Ii) As an easily accessible common light source, a green light-emitting diode (LED) was used ($\lambda$=530 nm with a FWHM of 30 nm and optical intensity≈0.02 mW/mm² on the sample surface).

Photodegradation of methylene blue as general photocatalytic quantification: We quantified photodegradation of methylene blue, resulting from ROS generated by mKate2 silk under green light activation. For mKate2 silk specimens, silk cocoon shells were punched into 5-mm-diameter discs with a thickness of ~400 µm. We prepared 15-mL methylene blue solutions (1 mL 0.05 wt. % methylene blue in 14 mL DI water) containing 12 silk discs (total weight=0.06 g). To reach the adsorption-desorption equilibrium in each test, the silk discs were stirred with 400 rpm in dark for two hours. While being stirred, the silk discs were irradiated by green light ($\lambda_{ex}$=532 nm and optical intensity≈0.2 mW/mm²) for four hours. Aliquots of 0.5 mL were collected repeatedly with a fixed time interval and the spectral absorption of methylene blue was measured using a fiber bundle-coupled spectrometer with a white-light tungsten halogen source. To exactly quantify the photocatalytic activity of mKate2 silk only, separate degradation tests of methylene blue were also carried out to factor out for two confounding effects: i) the adsorption of methylene blue to silk under a dark condition (i.e. no light irradiation) and ii) the photolysis of methylene blue without any silk discs due to the green light irradiation. For each elapsed irradiation time, a relative concentration $C_t/C_0$ of methylene blue was calculated using the absorption spectrum peak values at $\lambda$=668 nm normalized by the initial-time absorption value (FIG. 2A and FIG. 13). We estimated the reaction kinetics, following the apparent pseudo-first-order rate equation of Langmuir-Hinshelwood kinetics: $\ln(C_t/C_0)=-k_{app}t$, where $k_{app}$ is the rate constant (min⁻¹) and t is the irradiation time (Insets of FIG. 2A).

Bacterial inactivation as general detection of ROS: We tested ROS generated from mKate2 silk by inactivating Escherichia coli (E. coli) upon green light activation. We conducted four different groups of two different types of silk (i.e. white silk and mKate2 silk) and two light conditions (i.e. irradiation and unirradiation). We repeated these experiments for two different irradiation times of 30 and 60 minutes. Each bacterial inactivation experiment was performed in 3 assays with 4 replicates (n=12) in each group for statistical analyses. DH5α E. coli cells were grown in a Luria-Bertani (LB) medium at 37° C. in a shaking incubator to an optical density at 600 nm ($OD_{600}$) of 2.5 (~2×10⁹ cells/mL). The culture was diluted 10-fold and subsequently, white and mKate2 silk discs (diameter=6 mm) were placed on the culture. After incubation at 37° C. for 60 minutes, each silk disc was dried in dark for 30 minutes. For optical excitation of mKate2, the silk discs on a hydrated filter paper were irradiated with the green LED source ($\lambda_{ex}$=530 nm with a FWHM of 30 nm and optical intensity≈0.02 mW/mm²) for 30-60 minutes at the ambient room temperature, including white silk discs for comparisons. Without any irradiation, both white and mKate2 silk discs were kept in dark under the same conditions as two different control groups. After green light activation, each silk disc was transferred to a PBS of 1 mL and E. coli cells were eluted by shaking incubation for 60 minutes. To achieve a reasonable number of surviving cells for counting the colonies, the eluted cells were diluted up to 1000-fold, plated on the LB agar, and incubated overnight at 37° C. CFU from the mKate2 silk disc irradiated under weak green light for 60 minutes was clearly lower than that of the mKate2 silk disc in dark (FIG. 2B). Because our biological experiments carried four different groups, we conducted ANOVA and multiple comparisons tests. In particular, Duncan multiple comparison (two-sided) tests set a 5% level of significance for all pairs of means (six possible comparisons). The assumptions (i.e. normality and uniform variance) for the parametric analyses were tested. We performed the statistical analyses using Stata 14.2 (College Station, TX, USA).

Detection of superoxide and singlet oxygen using radical probe sensors: As free radical sensing probes of $O_2^{\cdot-}$ and $^1O_2$, we used TEMPO-9-ac (4-((9-Acridinecarbonyl) amino)-2,2,6,6-tetramethylpiperidin-1-oxyl) and ABDA (9,10-Anthracenediyl-bis(methylene)dimalonic acid), respectively. While in the original state of TEMPO-9-ac, acridine is quenched in the presence of nitroxide moiety, $O_2^{\cdot-}$ coverts nitroxide to the corresponding piperidine, which eliminates the quenching of the blue fluorophore. Thus, blue fluorescent emission from the acridine appears under ultraviolet light excitation ($\lambda_{ex} \approx 360$ nm and $\lambda_{em} \approx 440$ nm). The original state of ABDA emits fluorescence under ultraviolet light excitation ($\lambda_{ex} \approx 380$ nm and $\lambda_{em} \approx 431$ nm). Fluorescent signals of TEMPO-9-ac and ABDA were measured using a spectrometer. In this study, TEMPO-9-ac and ABDA were initially dissolved in DMSO and were diluted in PBS (pH 7.4), respectively, resulting in each solution containing 20-μM TEMPO-9-ac and 20-μM ABDA. In each measurement, 12 silk discs (diameter=5 mm and total weight=0.06 g) or regenerated silk films were immersed in a TEMPO-9-ac or ABDA solution with stirring of 400 rpm. Because water-soluble molecules are easily smeared inside silk fibers, the adsorption-desorption equilibrium was achieved prior to green light activation; the silk discs were kept in the solution with stirring of 400 rpm in a dark room for two hours at least. Turn-on fluorescent signals of TEMPO-9-ac solutions and turn-off fluorescent signals of ABDA solutions were spectrofluorimetrically monitored using a spectrometer ($\lambda_{ex}=365$ nm and $\lambda_{em}=400\text{-}550$ nm). Turn-on fluorescence (i.e. TEMPO-9-ac) from the silk discs was also imaged using a custom-build mesoscopic (between microscopic and macroscopic) imaging setup ($\lambda_{ex}=365$ nm and $\lambda_{em}=420\text{-}500$ nm) (see FIGS. 15A and 15B).

Detection of superoxide and singlet oxygen using fluorogenic scavengers: By detecting reduced photobleaching of mKate2 silk in the presence of $O_2^{\cdot-}$ and $^1O_2$ scavengers, we further validated the radical-based Type I and Type II reactions, because ROS contributes to photobleaching. In particular, we took advantage of TEMPO-9-ac and ABDA as physical quenchers or fluorogenic scavengers of $O_2^{\cdot-}$ and $^1O_2$, respectively. The photobleaching effect of mKate2 emission was reduced under green light irradiation in the presence of TEMPO-9-ac solution; the fluorescent emission was relatively maintained over the irradiation time ($\lambda_{ex}=532$ nm and optical intensity $\approx 0.2$ mW/mm$^2$) in the presence of the physical scavenger of $O_2^{\cdot-}$. Similarly, $^1O_2$ generation was detected by the maintained fluorescent intensity of mKate2 silk in the presence of ABDA. In addition, we confirmed reduced photobleaching rates of mKate2 using NBT and NaN$_3$, which are often used as a scavenger of $O_2^{\cdot-}$ and $^1O_2$, respectively (see FIGS. 17A and 17B).

Regeneration of mKate2 silk: To use the polymeric nature of silk, we regenerated mKate2 silk by extracting mKate2 silk fibroin from silk cocoon shells, minimizing heat-induced denaturation of mKate2. mKate2 silk cocoons were cut to pieces with sizes less than 5 mm and were heated for four hours at ~45° C. in an aqueous solution of 50-mM NaHCO$_3$ with alcalase (1.5 ml/L) with stirring of 400 rpm. Subsequently, the silk fibers were washed with deionized water (~35° C.) several times and were dried in ambient for 24 hours. Then, the silk fibers were completely dissolved in a 9.5-M LiBr solution with 1 mM DTT at 45° C. The dissolved solution was filtered through a miracloth and dialyzed with DI water for two days to remove the remaining the salt. The final concentration of mKate2 silk fibroin in the solution was ~4-5 (w/v) %. The solution was stored at 4° C. in dark before use. The fabrication process of the mKate2 silk solution was carried out under dark environment to minimize photobleaching of mKate2 in silk by room light. To form silk films, the solution was dried at 30° C. for 12 hours in an oven under dark.

Those having ordinary skill in the art will recognize that numerous modifications can be made to the specific implementations described above. The implementations should not be limited to the particular limitations described. Other implementations may be possible.

The invention claimed is:

1. A method of inactivating harmful microorganisms of a filtration
medium including pathogenic bacteria and viruses, comprising:
placing a predetermined quantity of a hybridized fluorescent silk on to a filtration medium;
applying light for a predetermined amount of time to the placed quantity of the hybridized fluorescent silk; and
passing a fluid through the medium, wherein the fluid is one of substantially air or substantially water,
wherein the hybridization is based on red fluorescent protein.

2. The method of claim 1, wherein the hybridized fluorescent silk is generated by adding fluorescent molecules or proteins during a silk polymer manufacturing process harvested from non-genetically engineered domesticated silkworms.

3. The method of claim 2, wherein the fluorescent molecules are porphyrin and porphyrin derivatives.

4. The method of claim 3, wherein the predetermined amount of time is based on a first order approximation governed by $Y=-mX+b$, where
Y is E. coli colony-forming unit,
where the slope is about −752.57, and
a starting point of about 141884.

5. The method of claim 1, wherein the predetermined amount of time is based on pathogen types, concentrations, irradiation light intensity, and wavelength range of the light.

6. The method of claim 5, wherein the predetermined amount of time is at least about 60 minutes for E. coli for a green light having a wavelength of about 530 nm with a Full width at half maximum (FWHM) of about 30 nm and an optical intensity of about 0.02 mW/mm$^2$.

7. The method of claim 1, wherein the filtration medium is one of an air filtration membrane, a bandage, a mask, a surgical outfit, a personal protective equipment (PPE), a seat fabric, a wallpaper, material usable as a wearable item, or any combination thereof.

8. The method of claim 1, wherein the hybridized fluorescent silk is applied as an ointment.

9. The method of claim 1, wherein the red fluorescent protein is one of KillerRed, SuperNova, KillerOrange, Dronpa, TurboGFP, mCherry, or any combination thereof.

10. The method of claim 1, wherein the red fluorescent protein is mKate2.

* * * * *